United States Patent
Fleck et al.

(10) Patent No.: US 9,672,397 B2
(45) Date of Patent: Jun. 6, 2017

(54) APPARATUS AND METHODS FOR MONITORING OBJECTS IN A SURGICAL FIELD

(71) Applicant: Stryker Combo L.L.C., Bingham Farms, MI (US)

(72) Inventors: Steven J. Fleck, Pittsburgh, PA (US); David Szakelyhidi, Pittsburgh, PA (US); Gautam Gandhi, Clarksburg, NJ (US)

(73) Assignee: STRYKER COMBO L.L.C., Bingham Farms, MI (US)

( * ) Notice: Subject to any disclaimer, the term of this patent is extended or adjusted under 35 U.S.C. 154(b) by 0 days.

(21) Appl. No.: 15/051,257

(22) Filed: Feb. 23, 2016

(65) Prior Publication Data

US 2016/0171262 A1    Jun. 16, 2016

Related U.S. Application Data

(60) Continuation of application No. 14/629,106, filed on Feb. 23, 2015, now Pat. No. 9,530,036, which is a
(Continued)

(51) Int. Cl.
*G06F 19/00* (2011.01)
*G06K 7/10* (2006.01)
(Continued)

(52) U.S. Cl.
CPC ......... *G06K 7/10425* (2013.01); *A61B 5/742* (2013.01); *A61B 5/746* (2013.01);
(Continued)

(58) Field of Classification Search
CPC ............................................. G06K 2017/0045
(Continued)

(56) References Cited

U.S. PATENT DOCUMENTS 3,367,431 A    2/1968    Baker
3,675,190 A    7/1972    Auer, Jr. et al.
(Continued)

FOREIGN PATENT DOCUMENTS

DE    102005049268 A1    4/2007
FR    2848701 A    6/2004
(Continued)

OTHER PUBLICATIONS

Indala Corp. Brochure on RF Tags; 1993.
(Continued)

*Primary Examiner* — Seung Lee
(74) *Attorney, Agent, or Firm* — Howard & Howard Attorneys PLLC

(57) ABSTRACT

Apparatus and methods for identifying and counting objects having identifiers entering and exiting a surgical field are provided. In one embodiment, the apparatus has an entry scanner, a hand held scanner and an exit scanner for generating a detection field and for receiving data which identifies said objects. In another embodiment, the apparatus has a plurality of lower antennas and an upper antenna for generating a detection field and for receiving data which identifies said objects. Various surgical devices with identifiers and methods for preventing electromagnetic coupling between and protecting objects and identifier are also provided. The invention further provides apparatus and methods comprising a handheld scanner and a mat adapted to underlie a patient during a surgical procedure.

20 Claims, 37 Drawing Sheets

Related U.S. Application Data division of application No. 13/927,467, filed on Jun. 26, 2013, now Pat. No. 8,985,446, which is a continuation of application No. 13/597,817, filed on Aug. 29, 2012, now Pat. No. 8,479,989, which is a continuation of application No. 13/041,996, filed on Mar. 7, 2011, now Pat. No. 8,256,674, which is a division of application No. 11/901,094, filed on Sep. 13, 2007, now Pat. No. 8,181,860.

(60) Provisional application No. 60/844,175, filed on Sep. 13, 2006.

(51) Int. Cl.

| | | |
|---|---|---|
| A61G 13/10 | (2006.01) | |
| H01Q 1/22 | (2006.01) | |
| G06K 7/01 | (2006.01) | |
| G06Q 10/08 | (2012.01) | |
| A61B 5/00 | (2006.01) | |
| A61F 13/44 | (2006.01) | |
| A61B 50/10 | (2016.01) | |
| A61B 50/13 | (2016.01) | |
| A61B 50/30 | (2016.01) | |
| A61B 50/36 | (2016.01) | |
| A61B 46/00 | (2016.01) | |
| A61B 90/90 | (2016.01) | |
| A61B 90/98 | (2016.01) | |
| A61B 17/00 | (2006.01) | |
| A61G 7/05 | (2006.01) | |
| A61G 13/12 | (2006.01) | |
| G06K 17/00 | (2006.01) | |
| A61B 50/00 | (2016.01) | |
| A61B 90/00 | (2016.01) | |
| A61B 50/37 | (2016.01) | |

(52) U.S. Cl.
CPC .............. *A61B 46/00* (2016.02); *A61B 50/10* (2016.02); *A61B 50/13* (2016.02); *A61B 50/30* (2016.02); *A61B 50/36* (2016.02); *A61B 90/37* (2016.02); *A61B 90/90* (2016.02); *A61B 90/98* (2016.02); *A61F 13/44* (2013.01); *A61G 13/10* (2013.01); *G06K 7/01* (2013.01); *G06K 7/10316* (2013.01); *G06K 7/10386* (2013.01); *G06K 7/10475* (2013.01); *G06Q 10/087* (2013.01); *G06Q 10/0875* (2013.01); *H01Q 1/2216* (2013.01); *A61B 50/37* (2016.02); *A61B 2017/00199* (2013.01); *A61B 2050/0056* (2016.02); *A61B 2050/0065* (2016.02); *A61B 2090/0805* (2016.02); *A61G 7/0502* (2013.01); *A61G 13/12* (2013.01); *A61G 2205/10* (2013.01); *G06K 2017/0045* (2013.01)

(58) Field of Classification Search
USPC .......................................................... 235/385
See application file for complete search history.

(56) References Cited

U.S. PATENT DOCUMENTS

| | | |
|---|---|---|
| 3,941,132 A | 3/1976 | Lenaghan |
| 3,965,907 A | 6/1976 | Hardy et al. |
| 4,039,827 A | 8/1977 | Zdrok et al. |
| 4,098,728 A | 7/1978 | Rosenblatt |
| 4,114,601 A | 9/1978 | Abeis |
| 4,193,405 A | 3/1980 | Abeis |
| 4,213,197 A | 7/1980 | Magori |
| 4,244,369 A | 1/1981 | McAvinn et al. |
| 4,264,575 A | 4/1981 | Zimmerman et al. |
| 4,289,032 A | 9/1981 | Tominaga et al. |
| 4,295,537 A | 10/1981 | McAvinn et al. |
| 4,361,231 A | 11/1982 | Patience |
| 4,422,548 A | 12/1983 | Cheesman et al. |
| 4,477,256 A | 10/1984 | Hirsch |
| 4,498,076 A | 2/1985 | Lichtblau |
| 4,510,489 A | 4/1985 | Anderson, III et al. |
| 4,625,731 A | 12/1986 | Quedens et al. |
| 4,626,251 A | 12/1986 | Shen |
| 4,639,253 A | 1/1987 | Dyer et al. |
| 4,645,499 A | 2/1987 | Rupinskas |
| 4,650,464 A | 3/1987 | Ruiz et al. |
| 4,658,818 A | 4/1987 | Miller, Jr. et al. |
| 4,711,996 A | 12/1987 | Drexier |
| 4,718,897 A | 1/1988 | Elves |
| 4,773,492 A | 9/1988 | Ruzumna |
| 4,832,198 A | 5/1989 | Aikhan |
| 4,887,715 A | 12/1989 | Spahn et al. |
| 4,889,230 A | 12/1989 | Zachry |
| 4,903,837 A | 2/1990 | Duello |
| 4,917,694 A | 4/1990 | Jessup |
| 4,922,922 A | 5/1990 | Pollock et al. |
| 4,943,939 A | 7/1990 | Hoover |
| 4,978,335 A | 12/1990 | Arthur, III |
| 5,009,275 A | 4/1991 | Sheehan |
| 5,031,642 A | 7/1991 | Nosek |
| 5,041,103 A | 8/1991 | Rupinskas |
| 5,045,080 A | 9/1991 | Dyer et al. |
| 5,049,219 A | 9/1991 | Johns et al. |
| 5,057,095 A | 10/1991 | Fabian |
| 5,103,210 A | 4/1992 | Rode et al. |
| 5,105,829 A | 4/1992 | Fabian et al. |
| 5,107,862 A | 4/1992 | Fabian et al. |
| 5,112,325 A | 5/1992 | Zachry |
| 5,186,322 A | 2/1993 | Harreld et al. |
| 5,188,126 A | 2/1993 | Fabian et al. |
| 5,190,059 A | 3/1993 | Fabian et al. |
| 5,227,765 A | 7/1993 | Ishizuka et al. |
| 5,231,273 A | 7/1993 | Caswell et al. |
| 5,300,120 A | 4/1994 | Knapp et al. |
| 5,329,944 A | 7/1994 | Fabian et al. |
| 5,353,011 A | 10/1994 | Wheeler et al. |
| 5,357,240 A | 10/1994 | Sanford et al. |
| 5,374,813 A | 12/1994 | Shipp |
| 5,381,137 A | 1/1995 | Ghaem et al. |
| 5,382,784 A | 1/1995 | Eberhardt |
| 5,443,082 A | 8/1995 | Mewburn |
| 5,456,718 A | 10/1995 | Szymaitis |
| 5,460,178 A | 10/1995 | Hudon et al. |
| 5,491,468 A | 2/1996 | Everett et al. |
| 5,610,811 A | 3/1997 | Honda |
| 5,629,498 A | 5/1997 | Pollock et al. |
| 5,637,850 A | 6/1997 | Honda |
| 5,650,596 A | 7/1997 | Morris et al. |
| 5,678,569 A | 10/1997 | Chew et al. |
| 5,689,239 A | 11/1997 | Turner et al. |
| 5,923,001 A | 7/1999 | Morris et al. |
| 5,931,824 A | 8/1999 | Stewart et al. |
| 5,991,728 A | 11/1999 | DeBusk et al. |
| 6,026,818 A | 2/2000 | Blair et al. |
| 6,339,732 B1 * | 1/2002 | Phoon ................... A61J 7/0084 |
| | | 700/237 |
| 6,366,206 B1 | 4/2002 | Ishikawa et al. |
| 6,626,445 B2 | 9/2003 | Murphy et al. |
| D486,915 S * | 2/2004 | Warschewske ............. D24/185 |
| 6,777,623 B2 | 8/2004 | Ballard |
| 6,861,954 B2 | 3/2005 | Levin |
| 6,933,849 B2 | 8/2005 | Sawyer |
| 6,998,541 B2 | 2/2006 | Morris et al. |
| 7,253,717 B2 | 8/2007 | Armstrong et al. |
| 7,253,736 B2 | 8/2007 | Tethrake et al. |
| 7,256,696 B2 | 8/2007 | Levin et al. |
| 7,362,228 B2 | 4/2008 | Nycz et al. |
| 7,420,468 B2 | 9/2008 | Fabian et al. |
| 7,496,521 B1 | 2/2009 | Louie et al. |
| 7,541,933 B2 | 6/2009 | Volpi et al. |
| 7,557,710 B2 | 7/2009 | Sanchez et al. |
| 7,633,392 B2 | 12/2009 | Neuwirth |
| 7,639,139 B2 | 12/2009 | Tafas et al. |

(56) References Cited

U.S. PATENT DOCUMENTS

| | | |
|---|---|---|
| 7,703,674 B2 | 4/2010 | Stewart et al. |
| 7,760,097 B2 * | 7/2010 | Volpi ................ G06K 7/0008 340/572.1 |
| 7,795,491 B2 | 9/2010 | Stewart et al. |
| 8,063,760 B2 | 11/2011 | Volpi et al. |
| 8,948,279 B2 | 2/2015 | Volpi et al. |
| 8,985,446 B2 | 3/2015 | Fleck et al. |
| 2001/0026946 A1 | 10/2001 | Asher |
| 2001/0034530 A1 * | 10/2001 | Malackowski ........ A61B 34/20 606/130 |
| 2002/0049650 A1 | 4/2002 | Reff |
| 2002/0067263 A1 | 6/2002 | Tofoya et al. |
| 2002/0143320 A1 | 10/2002 | Levin |
| 2004/0113787 A1 | 6/2004 | Smith |
| 2004/0199072 A1 | 10/2004 | Sprouse et al. |
| 2004/0250819 A1 | 12/2004 | Blair et al. |
| 2005/0101905 A1 | 5/2005 | Merry |
| 2006/0025668 A1 | 2/2006 | Peterson et al. |
| 2006/0028392 A1 | 2/2006 | Coveley |
| 2006/0044137 A1 | 3/2006 | Morris et al. |
| 2006/0106368 A1 | 5/2006 | Miller et al. |
| 2006/0241396 A1 | 10/2006 | Fabian et al. |
| 2007/0247318 A1 | 10/2007 | Pempsell et al. |
| 2008/0024278 A1 | 1/2008 | Volpi et al. |

FOREIGN PATENT DOCUMENTS

| | | |
|---|---|---|
| GB | 884143 A | 12/1961 |
| WO | 8909563 A1 | 10/1989 |
| WO | 9305707 A1 | 4/1993 |
| WO | 9422580 A1 | 10/1994 |
| WO | 9527252 A1 | 10/1995 |
| WO | 9604530 A1 | 2/1996 |
| WO | 9622510 A1 | 7/1996 |
| WO | 9729710 A1 | 8/1997 |
| WO | 9830166 A1 | 7/1998 |
| WO | 03073934 A1 | 9/2003 |
| WO | 03081379 A2 | 10/2003 |
| WO | 2005013496 A2 | 2/2005 |
| WO | 2006084021 A2 | 8/2006 |
| WO | 2006086603 A2 | 8/2006 |
| WO | 2007109234 A2 | 9/2007 |
| WO | 2008031630 A1 | 3/2008 |

OTHER PUBLICATIONS

Motorola/Indala Corporation Brochure; Indala RF/ID High-Performance Industrial Identification Tracking Control, Radio Frequency Identification Products; San Jose, CA; 99. 1-9; 1994.

PyMaH Corp. Brochure; Keep-a-Count Contain-Count Sponge System; 1989.

Texas Instruments Brochure on Transponders; Data Sheet No. 22-22-058; 1994.

Texas Instruments Brochure; Automatic Radio Frequency Identification System; 1994.

Texas Instruments Brochure; Read/Write Handheld Reader; Data Sheet No. 22-22-024; 1992.

* cited by examiner

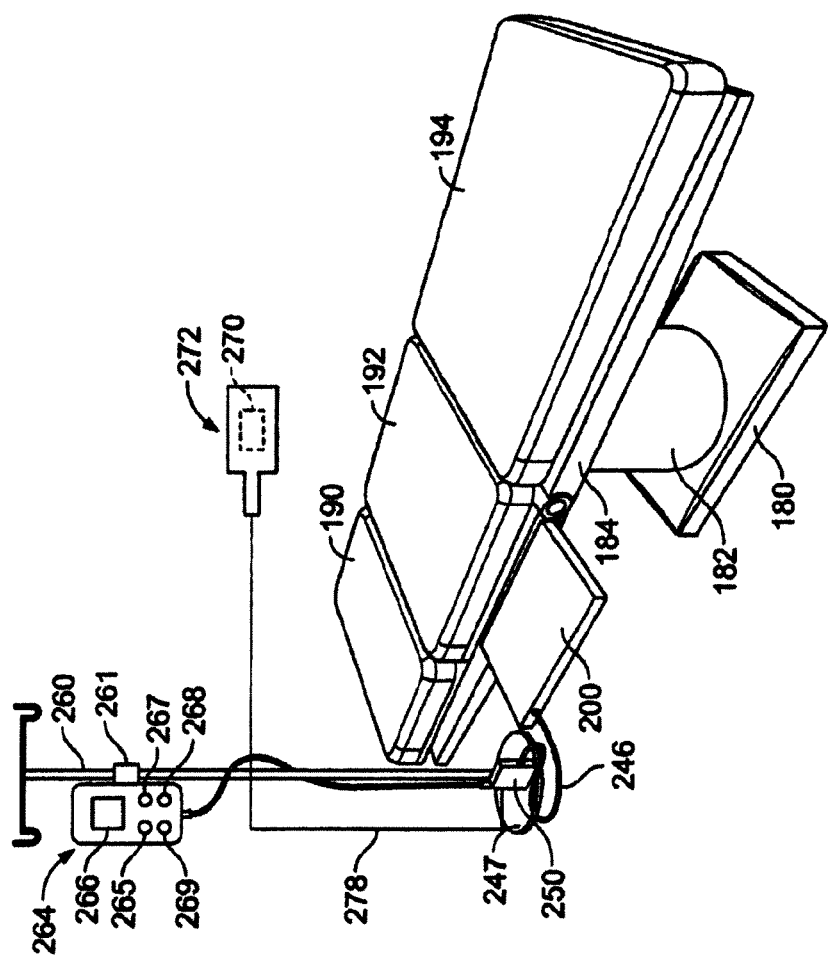

APPARATUS AND METHODS FOR MONITORING OBJECTS IN A SURGICAL FIELD

CROSS REFERENCE TO RELATED APPLICATIONS

This application is a continuation of U.S. patent application Ser. No. 14/629,106, filed Feb. 23, 2015, and entitled "Methods for Monitoring Objects in a Surgical Field," which is a divisional of U.S. patent application Ser. No. 13/927,467, filed Jun. 26, 2013, and entitled "Apparatus and Methods for Monitoring Objects in a Surgical Field," which is a continuation of U.S. patent application Ser. No. 13/597,817, filed Aug. 29, 2012, and entitled "Apparatus and Methods for Monitoring Objects in a Surgical Field," which is a continuation of U.S. patent application Ser. No. 13/041,996, filed Mar. 7, 2011, and entitled "Apparatus and Methods for Monitoring Objects in a Surgical Field," which is a divisional of U.S. application Ser. No. 11/901,094, filed Sep. 13, 2007, and entitled "Apparatus and Methods for Monitoring Objects in a Surgical Field," which claims the benefit of and priority to U.S. Provisional Application No. 60/844,175, filed Sep. 13, 2006, the entirety of each of which is herein incorporated by reference in their entirety.

BACKGROUND OF THE INVENTION

The present invention is directed toward apparatus and methods for monitoring the entry of objects into a surgical field and the exit therefrom and for monitoring a surgical patient to determine if any such objects are within the patient.

It is of critical importance that the entry of objects into a surgical field and into a surgical site, as well, as their removal be very carefully reconciled so as to avoid inadvertent retention of an object within a patient. Counting objects entering and exiting a surgical field is a conventional operating room procedure. Such practices greatly reduce the risk of an object being inadvertently retained within the patient. Such procedures typically involve the manual counting of objects entering and exiting the surgical field, as well as the visual examination of the surgical site. It is critical that such procedures be completed before the surgical site is closed. In the event that the surgical site needs to be closed with minimum delay, it is necessary to finish the verification that there is no object retained in the patient as quickly as possible. It is therefore desirable to provide effective and timely means and methods of monitoring objects entering and exiting a surgical field with a high degree of accuracy and with minimum effort from medical personnel.

SUMMARY OF THE INVENTION

Apparatus and methods are provided for monitoring objects having identifiers in a surgical field. Such objects may include surgical aids such as surgical sponges, surgical instruments such as scalpels and needles, medical supplies and other tools utilized by medical personnel in a surgical field such as writing instruments. Additional examples include items in the surgical field which may or may not be used in a surgical procedure. Other objects may include, for example, items worn by medical personnel or surgical patients such as watches, glasses, dentures, hearing aids, surgical scrubs caps, gloves and identity cards.

An identifier on an object to be monitored may be a radio frequency (RF) tag or a microchip that utilizes any other suitable technology to identify objects. Alternatively, an object may be equipped to spontaneously emit electromagnetic waves containing identification information, which may be read by antennas. A bar code may also be attached to an object in order to identify it. An object may also be identified using pattern recognition technology, whereby a visual image of the object is obtained, and control circuitry algorithms are utilized to identify the object from its image. Any other suitable identifier or combination of identifiers may also be used.

The apparatus may include an object entry detection zone and an object exit detection zone. The object entry detection zone may be adapted to receive new objects dispensed from a housing prior to introduction into a surgical field while the object exit detection zone may be adapted to receive used objects discarded into said housing after exit from said surgical field.

One or more scanners may be operatively associated with the object entry detection zone and the object exit detection zone, respectively. Said scanners may each contain one or more antennas which may detect an individual object or a plurality of objects substantially simultaneously, for example, by emitting a detection field within the detection zones. The antennas may also detect the objects after they have entered a recess, for example, by emitting detection fields into the recess. A control circuitry may be operatively associated with the scanners for controlling the operation of the scanners.

Various approaches to controlling the signals emitted from the antennas are provided. In one embodiment, all of the antennas are powered, and the control circuitry controls the tuning and detuning of the antennas such that when one antenna is tuned, the others are detuned. Another embodiment involves powering one antenna tuned to a specific resonant frequency during a period of operation while the other antennas are unpowered. In yet another embodiment, control is effected by switching both the powering and tuning of the antennas.

In a further embodiment, one antenna emits a signal out-of-phase with respect to the signals from at least one other antenna. A further embodiment utilizes the mechanical movement of one antenna with respect to other antennas.

In another embodiment, the invention further provides a plurality of antennas preferably disposed within a housing or mat so as to underlie at least a portion of the patient undergoing a surgical procedure for emitting detection fields upwardly and for detecting objects within the patient or otherwise in or around the surgical site. A further refinement of this embodiment involves an upper antenna which may be in a handheld device helping to direct the detection field. In one embodiment, the upper antenna may provide a loop surrounding the surgical site.

Various approaches to protecting identifiers from deterioration and data corruption are provided. In certain embodiments, identifiers may be wrapped or encapsulated in protective casing.

Various approaches to preventing electromagnetic coupling between identifiers are also provided. In one embodiment, identifiers may be positioned at strategic locations on objects that increases the distances between the identifiers, and objects may be packaged in a specific order. In another embodiment, objects may be wrapped or encapsulated in protective casing.

BRIEF DESCRIPTION OF THE DRAWINGS

FIG. 14 is an illustration of another embodiment of the invention wherein a plurality of antennas is positioned under the patient.

DETAILED DESCRIPTION OF THE INVENTION

As employed herein, the term "patient" means a member of the animal kingdom including humans.

As employed herein, "surgical site" means the portion of the patient's body where the surgery will be or has been performed and adjacent portions of the surgical table or bed supporting the patient.

As employed herein, "surgical field" means the sterile environment which includes the patient, equipment and personnel which will be or might be employed during a surgical procedure.

As employed herein, the term "non-optical" refers to a method or system that does not require the use of line-of-sight visible light.

As employed herein, the term "object in a surgical field" or "object" refers to objects found in the sterile, environment which includes the patient, equipment and personnel which will be or might be employed during a surgical procedure.

Figure 1:
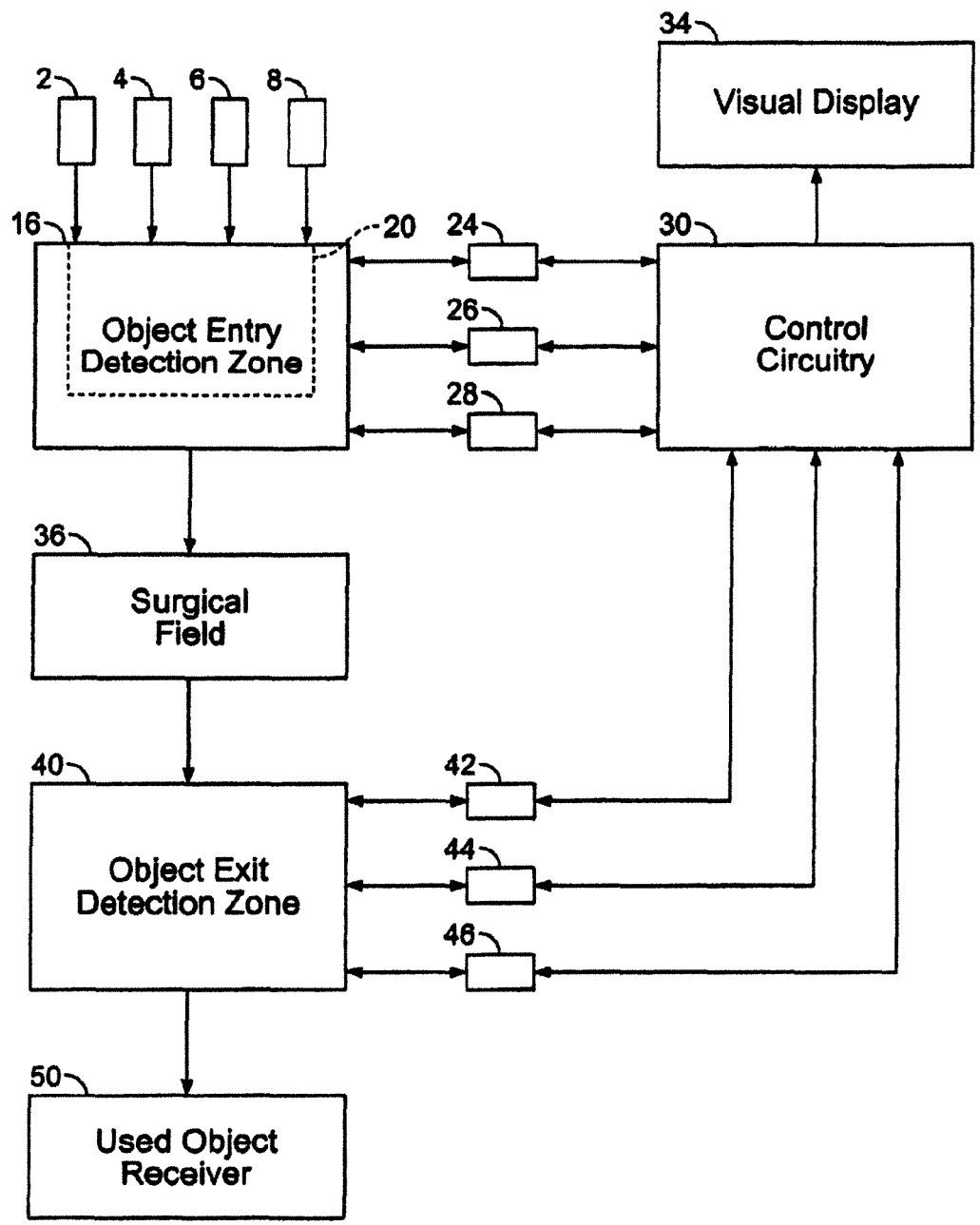
FIG. 1 is a schematic illustration of a form of system of one embodiment of the invention.
Figure 2:
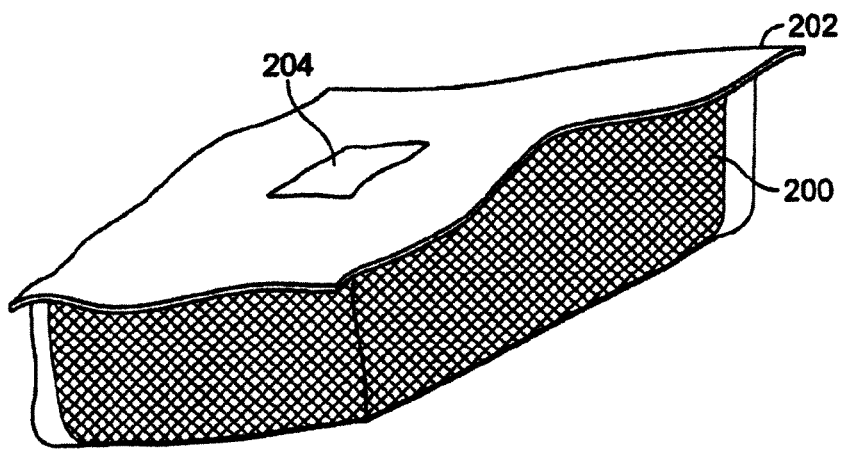
FIG. 2 shows a package of objects of one embodiment of the invention.

Referring to FIG. 1, there is shown a plurality of objects 2, 4, 6 and 8, each equipped with an identifier (not shown) which may distinguish each object from the others in the group. Objects 2, 4, 6 and 8 may be contained in individual packages. If objects 2, 4, 6 and 8 have packages, identifiers may be placed either directly on the object or on the outside of the object's package. For example, FIG. 2 shows packaging 202 which can contain any suitable number of objects. An identifier 204 is placed on packaging 202 in order to identify packaging 202. The identifier may include a numerical identifier, an alphabetical identifier or an alpha-numeric identifier. Furthermore, certain additional information may be provided on the identifier such as the specific type of object, the manufacturer, the plant where it was manufactured, the package identifier of a package which contains a plurality of individually identified objects, the total number of objects in a package and any other desired information.

If desired, the user may be able to differentiate between objects belonging to different packages. Different packages, each containing a plurality of objects, may each contain a package identifier that contains information on the objects within the packages, such as the number of objects in the package. The objects may also each contain their own unique identifier as well as a package identifier that unique to a package but is common among all items in a given package. The objects may also contain a quantity identifier that indicates the correct quantity of items that should be present in the package. The system may be set up to initially read a package identifier and quantity identifier from one or more of the tags in a package to determine the package identity and the number of objects that are supposed to be in the package. The system may then count the number of objects with the same package identifier by detecting the unique identifier of each object in the package. The system may compare the number of objects that are supposed to be in the package with the number of objects that are in the package in order to verify that that package is complete, before using the package in a surgical field. If the system detects that a package is incomplete, the user may be alerted that the package may be incomplete, or that identifiers on one or more objects in the package may be malfunctioning.

Control circuitry 30 may be programmed to take the package identifier and quantity data from an individual identifier in the exit detection zone and use this to add all of the remaining items not yet scanned by the exit detection zone from the same package to the list of items detected in the entry detection zone. Although the software does not yet have the unique identifiers for these items not yet scanned, it creates a placeholder for them. This provides a user who forgot to scan in a package with a more accurate representation of the surgical inventory than the user would otherwise have had. By using package identifier as well as quantity data, the software may prevent confusion in the case that another partial pack is discarded before being scanned in.

If desired, the user may be able to differentiate between objects belonging to different packages. Different packages, each containing a plurality of objects, may each contain a package identifier that contains information on the objects within the packages, such as the number of objects in the package. The objects may also each contain their own unique identifier. The system may be set up to initially read a package identifier to detect the number of objects that are supposed to be in the package. The system may then count the number of objects with the same package identifier by detecting the unique identifier of each object in the package. The system may compare the number of objects that are supposed to be in the package with the number of objects that are in the package in order to verify that that package is complete, before using the package in a surgical field. If the system detects that a package is incomplete, the user may be alerted that the package may be incomplete, or that identifiers on one or more objects in the package may be malfunctioning.

In one embodiment, when these objects enter a detection field, the identifiers may emit responsive data thereby enabling the system, in the manner to be described hereinafter, to identify the specific object which is in the field. The identifier may be any suitable identifier such as one with an integrated circuit and an antenna (e.g., a copper wire loop or printed circuit antenna). This may enable the system to identify the specific type of object, to count the objects and to confirm the presence of the object on an individual basis or substantially simultaneously for a plurality of objects.

The identifiers on the objects may also be programmed as they are read. They may be assigned a unique number from a predetermined list of numbers or from a random number generator. Utilizing a random number generator achieves the same goal as utilizing a predetermined list of numbers. The manufacturer may also provide information regarding the date and location of manufacturing as well as other identifying information.

The identifiers on an object may also be programmed with information about the object's treatment history, such as, for example, sterilization of the object. For example, when an object is sterilized, its identifier may be programmed with information such as the date of sterilization, the particular process used for sterilization, the date of expiration of the sterility of the object and other desirable information. When an object is received in the object entry detection zone 16, the system may check the date of expiration of the sterility. The user may be alerted if the sterility of the object has expired. Additionally, the system may decode encrypted information, stored on the identifier, that identifies the particular sterilization process used on that item, and may issue a warning or take other appropriate action if the object was not sterilized using a validated sterilization process.

The objects 2, 4, 6 and 8 may be received in the object entry detection zone 16 sequentially or simultaneously. A plurality of antennas 24, 26 and 28 may be operatively associated with (e.g., coupled to) the object entry detection zone 16 to detect and read data from the identifiers. The antennas 24, 26 and 28 may establish a field within recess 20, and may thereby facilitate determining the identity of each object entering the object entry detection zone 16. The data received by the antennas 24, 26 and 28 may be delivered to control circuitry 30 which may record data regarding each object entering the object entry detection zone 16. The control circuitry 30 may also function as a controller to provide energizing power to antennas 24, 26 and 28 and to control operation thereof in respect of various parameters and in the proper sequence to permit substantially simultaneous identification of a plurality of objects. A visual display unit 34 may be controlled by control circuitry 30 and may provide a visual display with whatever information is desired regarding each object 2, 4, 6 and 8 being introduced into the object entry detection zone 16.

While the system may employ a plurality of antennas at the entry detection zone 16 and the exit detection zone 40, such as the three antennas 24, 26 and 28 shown in FIG. 1, the system may alternatively be employed with a single antenna in the entry detection zone 16 or exit detection zone 40, if desired. Identifier orientation with respect to the antenna may then become more important. In this latter case, it may be preferable to place the identifier of the object flat against the antenna. The manufacturer could create the identifiers with a consistent desired known flat configuration to facilitate uniform size, shape and positioning within a single or multiple packages of objects intended for use in a single antenna system.

In operation, the objects 2, 4, 6 and 8 may be delivered, either manually or by another means, from the object entry detection zone 16 into the surgical field 36. At that point, the control circuitry may have a record of each specific object that has entered into the surgical field 36. The user may detect one object at a time or a plurality of objects simultaneously. If the user desires to detect only one object at a time, the system may produce an error message if more than one object is detected simultaneously.

Objects that are employed within the surgical field may be introduced into the object exit detection zone 40 after use. The object exit detection zone 40 may be coupled with a plurality of antennas 42, 44 and 46. The antennas 42, 44 and 46 may generate a detection field within the object exit detection zone 40 such that specific identification of each identifier on each object is provided. This may be accomplished in a manner to be described hereinafter for a plurality of objects simultaneously. The data received may be delivered to control circuitry 30 for comparison and storage therein with the output being shown on the visual display 34. The visual display 34 may be provided with controls which may permit simultaneous display of object entry data and object exit data as well as other desired information.

A single object or package of objects may be introduced into the object entry zone 16, which may be provided with a single antenna or a plurality of antennas, such as antennas 24, 26 and 28. It may not be necessary to remove the individual objects from the package in order to have the identifier of each object read. Two or more antennas may be used so that the orientation of the objects and, therefore, the orientation of the identifiers need not be controlled with respect to the antennas. Using two or more antennas that may be scanned using non-optical means may also ensure a reading regardless of the depths of objects within the body of a patient. For example, each antenna may be positioned at a different location along the body of the patient, thereby ensuring that a wide reading range is covered.

If desired, the object entry detection zone 16, rather than being a separate structure, may be provided at the discharge end of an object dispenser such as a sponge dispenser. In this embodiment, the system may function as with the object entry zone 16 and may have withdrawal of the object from the storage container serving as the act triggering detection.

If desired, the control circuitry 30 may be so structured as to permit a user to insert a request for a predetermined number of objects to be dispensed automatically from the storage container under control of the control circuitry. The control circuitry may then store information from the identifiers on the objects regarding the act of dispensing and the specific unique identifying information of the object being dispensed, as well as the count of dispensed objects.

The control circuitry 30 may also store other information about an object such as its weight. In one embodiment, entry detection zone 16 and exit detection zone 40 in FIG. 1 may be equipped with scales (not shown) for weighing objects such as surgical sponges. Upon entry into the object entry detection zone 16, an object may be weighed, and its initial dry weight recorded by control circuitry 30. After being used and upon entry into the object exit detection zone 40, the object may be weighed again, and its final weight recorded by control circuitry 30. Control circuitry 30 may compare the initial and final weights in order to determine the total amount of blood or fluid that has been removed from the patient onto said object.

The function and data integrity of identifiers may be verified at the object entry and exit detection zones. In one embodiment, when an object enters the entry detection zone or the exit detection zone, control circuitry 30 be may used to compare the data read from the object's identifier with data pre-programmed into control circuitry 30. If the data on the object's identifier does not match the data pre-programmed into control circuitry 30, the user may be alerted. This may ensure that all identifiers are functional. In another embodiment, control circuitry 30 may be programmed to detect identifiers that are malfunctioning, such as identifiers that may have become damaged during shipping or a package identifier that may have been manufactured with an incorrect number of objects. The user may be alerted about the occurrence of such malfunctioning identifiers. This may for example prevent the incorrect counting of objects or other errors.

Where multiple antennas such as antennas 24, 26, 28 or 42, 44, 46 cooperate with respect to a particular detection zone 16 or 40, it may be preferred that they function as individuals with the control circuitry 30 controlling the sequence and manner in which each antenna will function. For example, the control circuitry 30 may be structured to tune and detune the antennas within a group (24, 26, 28) (42, 44, 46) such that during a period of operation of one said antenna within a group, it is tuned to a specific resonant frequency, the remaining antennas of the group are detuned with respect to that frequency. Power may be supplied to only the antenna being tuned.

In another embodiment, one antenna may be powered to a specific resonant frequency during a period when the others are unpowered. In an alternate embodiment, one antenna may be caused to emit a signal out-of-phase with respect to the others. Mechanical movement of the antennas sequentially may be employed. The timing of each individual antenna's activation may vary, but may be on the order of about 250 to 1000 milliseconds per full cycle, for example. The antennas of each group (24, 26, 28) or (42, 44, 46) may be cycled in this manner so that each antenna will be subjected to each isolated parameter. Any suitable orientation of antennas, or a combination of orientation of antennas, may additionally be used.

Figure 4:
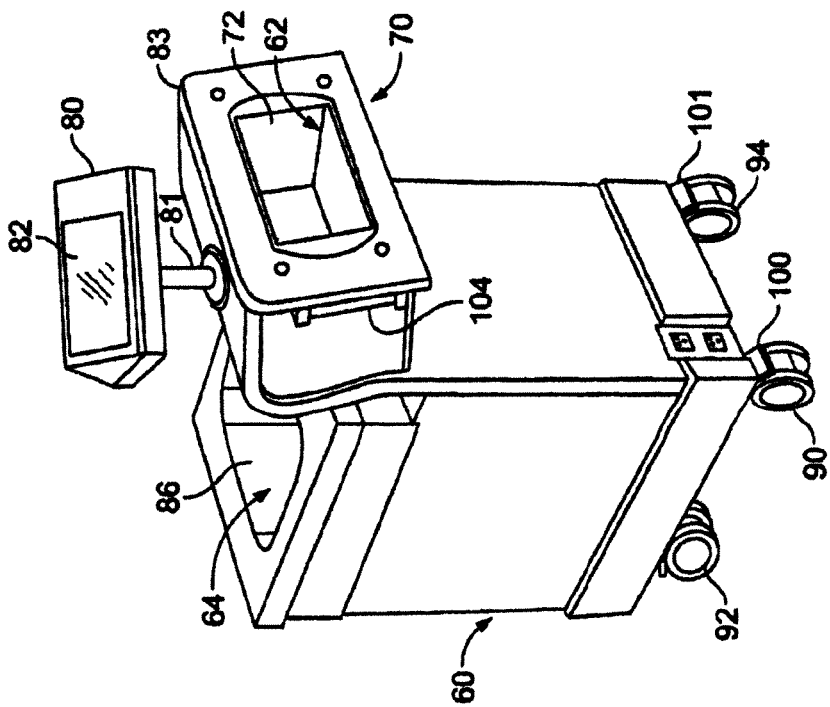
FIGS. 3 and 4 are perspective views taken from opposite sides of a unit illustrating a system containing both object entry and object exit units.
Figure 3:
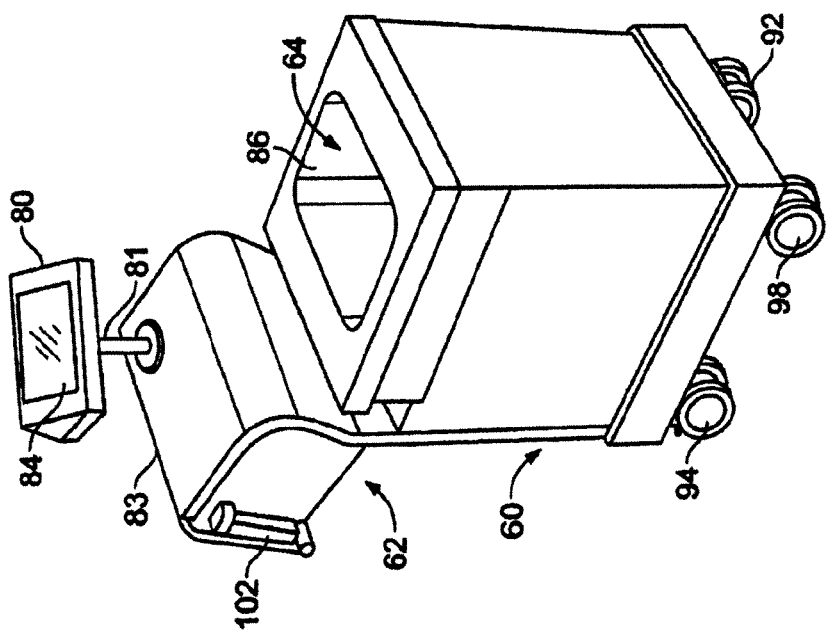
Figure 5:
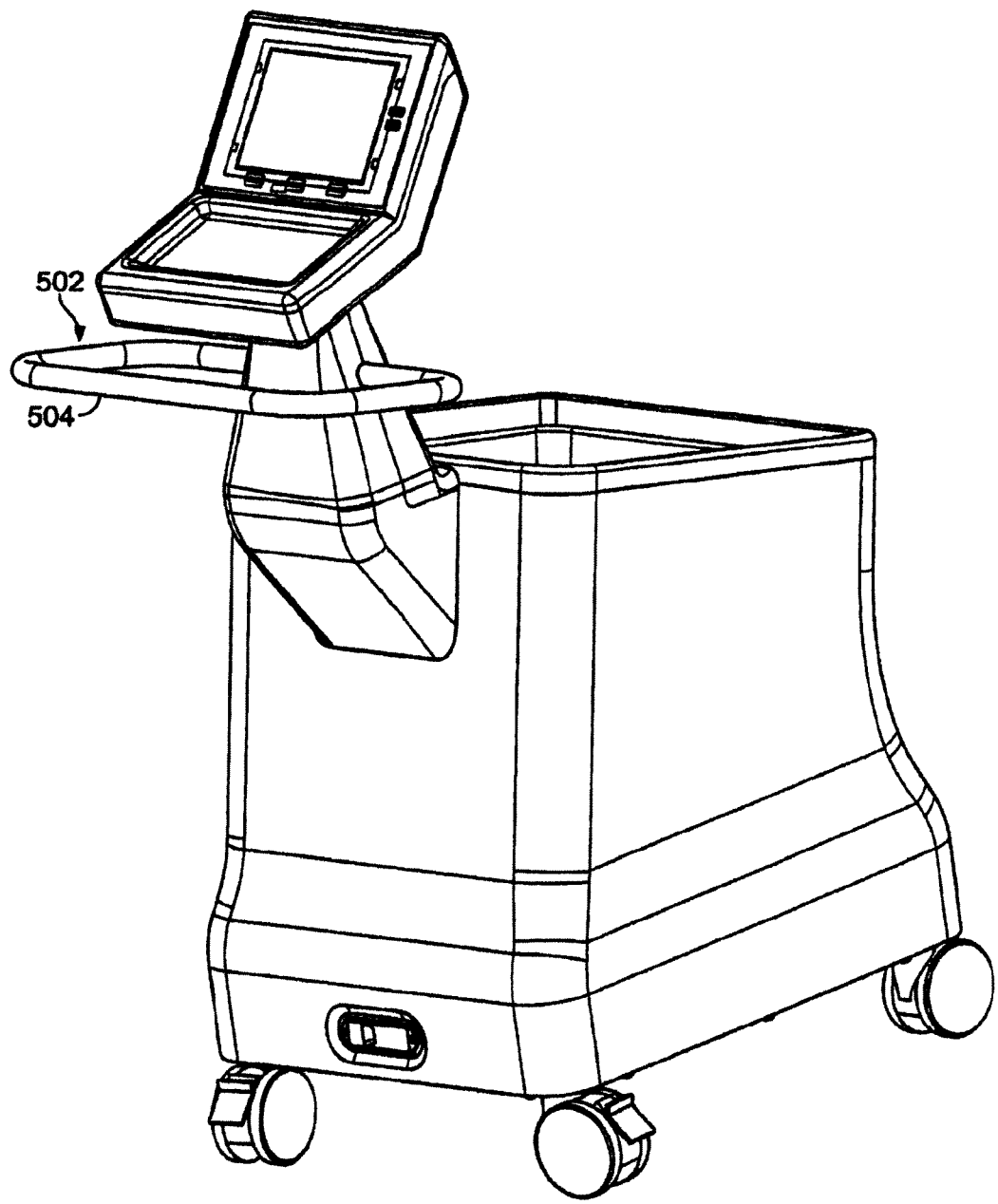
FIG. 5 is a schematic illustration of a form of system of one embodiment of the invention.

Referring to FIGS. 3 and 4, there are shown two perspective views of a cart 60 which, in the form shown, may contain both the object entry detection zone 62 and the object exit detection zone 64. Entry detection zone 62 may have an enclosure 70 defining an outwardly open recess 72 within which objects bearing identifiers may be introduced, either individually or in the original package. Alternatively, entry detection zone 62 may not have an enclosure. FIG. 5 shows one embodiment where a single antenna 504 (not shown) is located within a horizontally oriented entry zone 502. As shown in FIG. 5, the device has an LCD screen that is at a slight angle to vertical and a horizontally oriented entry zone 502 in which the entry zone antenna 504 lies at a slight angle to horizontal. It may be desirable to use a flat panel instead of an open recess when, for example, objects that may not fit into an open recess need to be introduced into the entry detection zone (e.g. a mat containing antennas, identifiers or both as discussed in connection with FIGS. 16a and 16b). Referring back to FIGS. 3 and 4, if a plurality of objects is within a single package, each object may have an identifier. The cart 60 may be positioned within the surgical field or closely adjacent thereto. Prior to introducing objects into the surgical site, the control circuitry, which may be within housing 80, in a manner to be described hereinafter, may monitor the unique identification of each object entering a detection zone and store that data. This may facilitate identification of the specific object, (i.e., its type and other characteristics) and also the count of objects entering the surgical field. Housing 80 may also contain a first visual display 82 for displaying data regarding objects processed through object entry detection zone 16 and object exit detection zone 64. A second visual display 84 may display the same data, but may permit viewing from the other side. The housing 80 may be supported on a post 81 which may be secured to the upper surface 83 of object entry detection zone 62. Visual displays 82 and 84 may, for example, be LCD displays or any other suitable displays.

Figure 6:
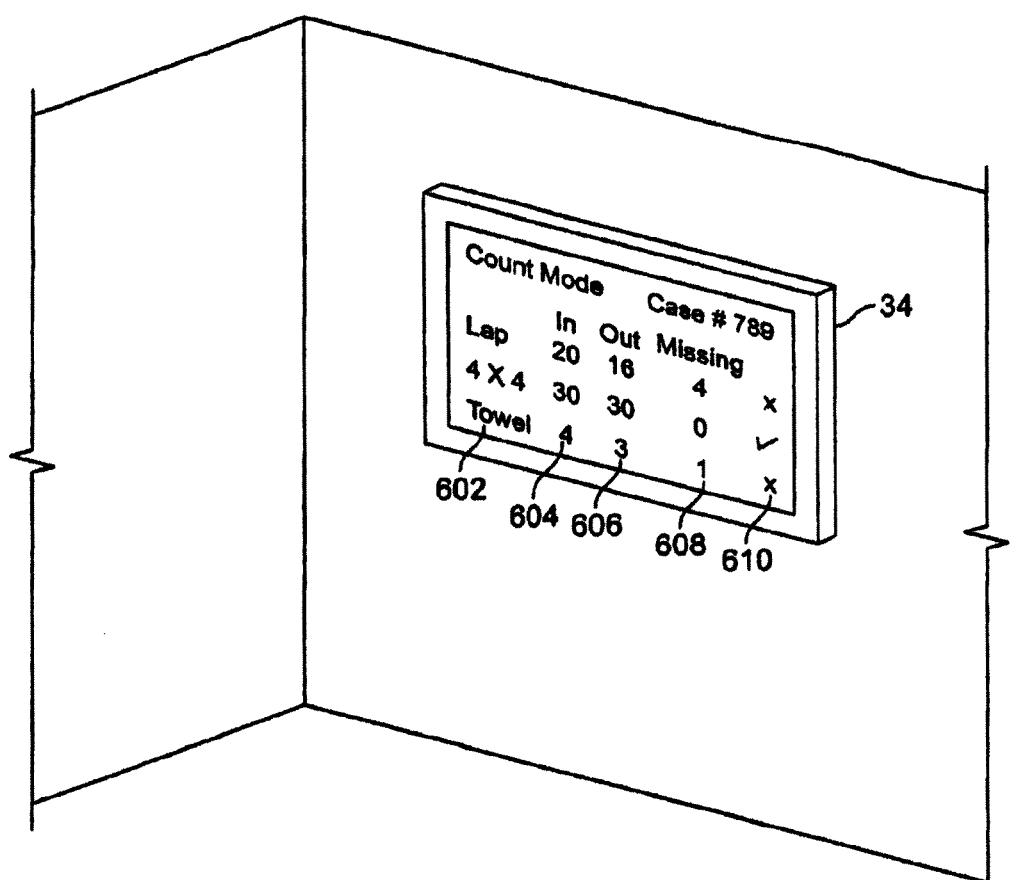
FIG. 6 shows a visual display of one embodiment of the invention.

Visual displays 82 and 84 may be unattached to housing 80. In another embodiment, visual displays 82 and 84 may be integrated into one visual display and may be a device separate from housing 80. For example, the visual display may be a wall-mounted display that communicates with control circuitry 30 through a wired or wireless connection. The visual display may be an LCD display or any other suitable display. FIG. 6 shows visual display 34 which is a wall-mounted display.

Objects that are withdrawn from the surgical site may be introduced into upwardly open recess 86 of the object exit detection zone 64 and may be identified and counted. Data regarding the objects may be displayed on screens 82 and 84 of housing 80. The objects which pass through exit detection zone 64 may then be received in a collection container (not shown) which may be removed from cart 60 to dispose of the objects in a safe manner. The collection container may be a plastic bag of suitable size and strength which may be removable and secured within upwardly open recess 86 (FIG. 3).

The displays 84, 82 and 34 in FIGS. 3, 4 and 6, respectively, may visually display the data regarding objects. For example, display 34 in FIG. 6 may show a chart having a first column 602 listing the objects in a surgical field, a second column 604 listing the objects entering the surgical field, a third column 606 listing the objects exiting the surgical field and a fourth column 610 providing a checkmark or "X" mark indicating whether or not the same number of a given object has entered and left the surgical field. In an alternative embodiment, the first column may list a specific object identity with the second column providing a checkmark, "X" mark or other indication showing that an object has entered the surgical field and a third column providing space for a checkmark, "X" mark or other indication showing that an object has exited the surgical field. Various other means of providing the desired information regarding the monitored objects entering and exiting the surgical field may be visually displayed on displays 84, 82 or 34 with or without desired additional information.

Referring to FIGS. 3 and 4, the object entry detection zone 62 and object exit detection zone 64 may each be structured to monitor a plurality of objects passing into respective zones 62 and 64 substantially simultaneously regardless of the orientation of the objects. The antennas may be designed, positioned and operated in such a manner to permit such simultaneous monitoring. Further, as the scanners may be of a non-optical type, the presence of blood, other body fluids or body tissues on the object or identifier will not interfere with obtaining accurate readings. The cart 60 in the form shown may have wheels 90, 92, 94 and 98 at the corners as well as manually-operated brakes 100, 101, each associated with one wheel 90 and 94. In the form shown, a pair of handles 102 and 104 are provided for facilitating movement of the cart 60. Such handles may be optionally used in conjunction with any embodiment of the invention.

The body of the cart housing may be made of any suitable materials that are structured to have the adequate strength to support the equipment, avoid interference with the functioning of the equipment and be capable of maintaining the cleanliness required in a surgical field. Suitable materials that may be used include resinous plastics, non-ferrous metals and medium-density fiberboard (MDF), to name a few.

Figure 8:
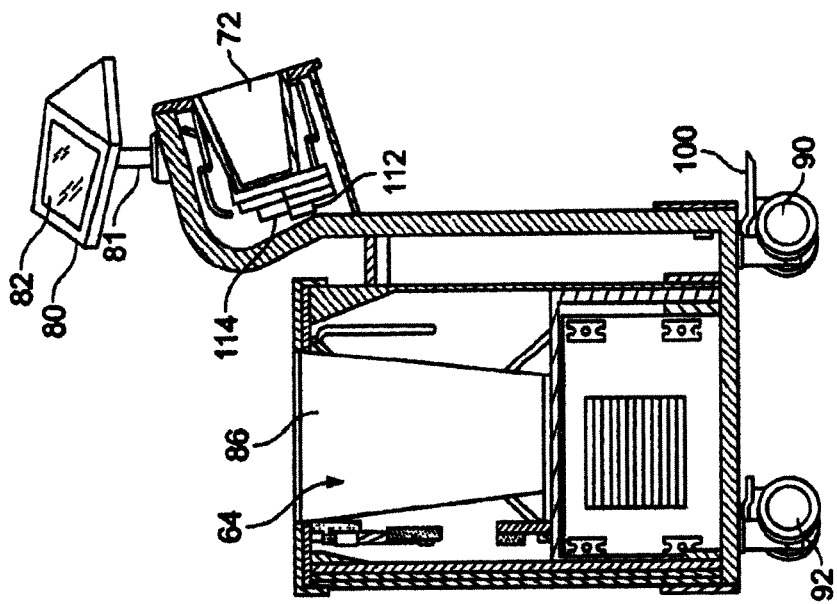
FIG. 8 is an elevational, cross-sectional illustration of the opposite side of the unit shown in FIG. 7.
Figure 7:
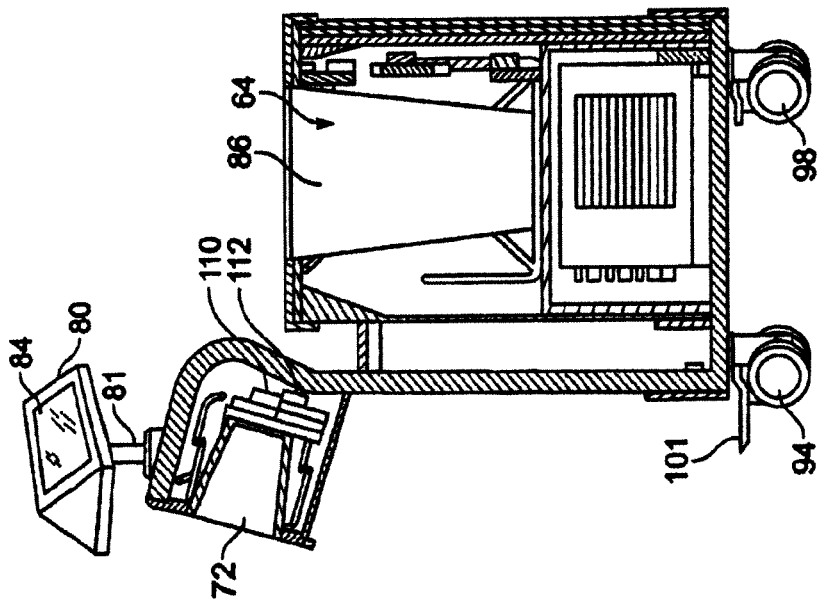
FIG. 7 is an elevational, cross-sectional illustration of one side of a unit of the type shown in FIGS. 3 and 4.
Figure 9:
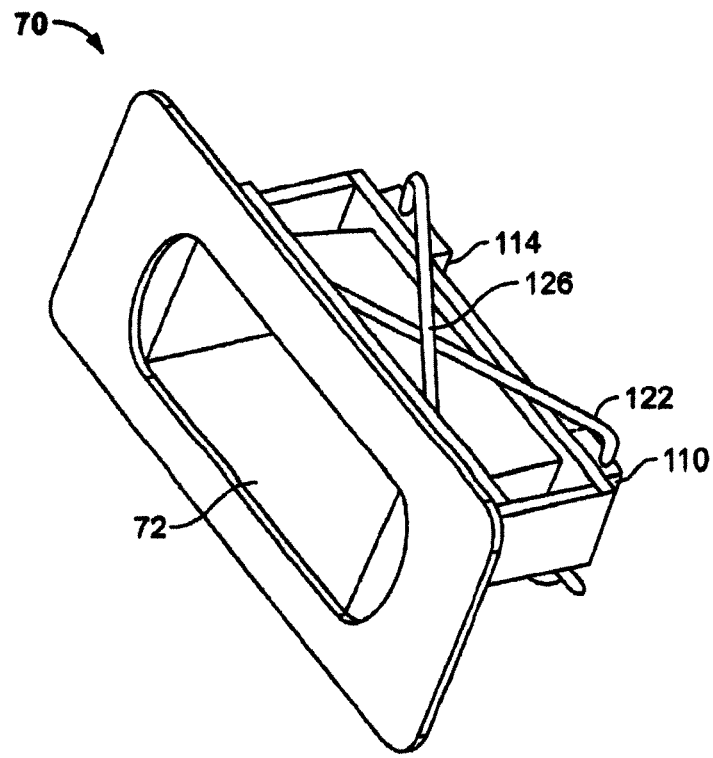
FIG. 9 is a perspective view of an intake system usable in the embodiment of FIGS. 1 through 8 showing the entry detection unit.
Figure 10:
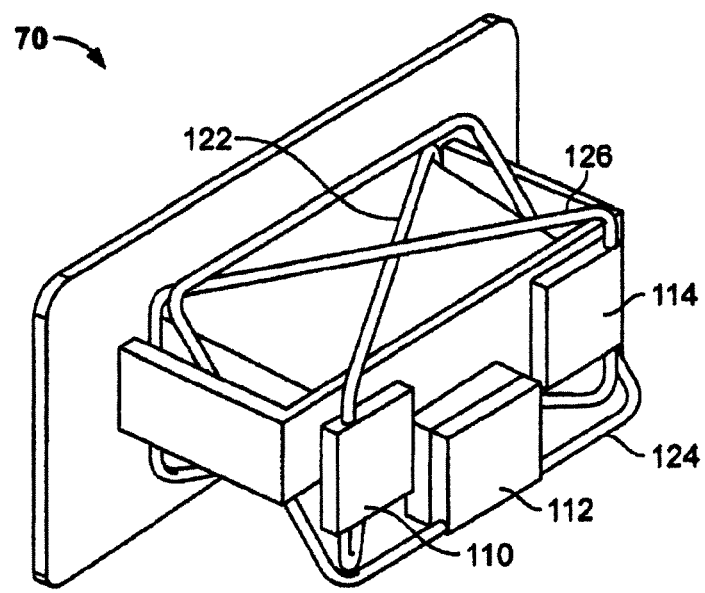
FIG. 10 is a perspective view of the entry detection unit of the system of FIGS. 1 through 8 taken generally from the rear thereof.

Referring to the cross-sectional illustrations of cart 60 of FIGS. 3 and 4 in FIGS. 7 and 8, there is shown the object entry detection zone 72 with the overlying visual display housing 80. Referring to FIGS. 7 through 10, a plurality of antenna tuning circuits 110, 112 and 114 which may be respectively operatively associated with antennas 122, 124 and 126, may be powered and controlled by control circuitry 30 of FIG. 1. A tuning circuit, such as tuning circuits 110, 112 and 114, may be in the form of a circuit board and may function to alter tuning to determine the resonant frequency of a specific antenna with which it is operatively associated. The antennas 122, 124 and 126 in the form shown may be made of rigid copper tubing and therefore be self-supporting. Other self-supporting or non-self-supporting materials with additional supports provided may alternatively be used. Each antenna 122, 124, 126 may be a closed loop which surrounds the recess 72 within which the objects are scanned.

The antennas 122, 124 and 126 need not be coplanar with each other and may rather be at an angle to each other. The tuning circuits 110, 112 and 114, while each operatively associated with an antenna 122, 124 and 126, respectively, may not need to have any particular orientation with respect to the other tuning circuits 122, 124 and 126. The antennas 122, 124 and 126 may be controlled by control circuitry 30 through tuning circuits 110, 112 and 114.

The control circuitry 30, in the form shown, may be disposed within visual display unit 80. The control circuitry 30 may control and coordinate the detection fields emitted by each successive antenna. As stated above, the control circuitry 30 may be structured to tune and detune the antennas such that during the period of operation, one antenna 122, 124 or 126 is tuned, while the other antennas are detuned. This may create a progression of detection fields and, with the data received back from the identifiers secured to each of the objects, may permit the control circuitry 30 to receive data from a plurality of objects substantially simultaneously (e.g., on the order of tens to hundreds of milliseconds or more, although typically not longer than several seconds) and regardless of object orientation. The tuned antenna in this embodiment may be tuned to a specific frequency with the remaining antennas being detuned as to that frequency. Each antenna may sequentially be tuned while the others are detuned.

An alternate approach to cycling the operation of the respective antennas 122, 124 and 126 may be to deliver power to the antennas such that one antenna, such as 122, is powered to a specific resonant frequency during a period of operation and the remaining antennas 124 and 126 are unpowered with respect to that frequency with successive stages resulting in each antenna 122, 124 and 126 being tuned to the desired resonant frequency, while the others are detuned.

In one embodiment, only a single antenna of the group of the plurality of antennas may be powered at a time and only that antenna may be tuned at that time with the rest being unpowered and detuned. After that, another antenna may be powered and tuned with the rest being unpowered and detuned until the complete cycle involving simultaneously powering and tuning an individual antenna is accomplished. An unpowered antenna, while still tuned, can nevertheless pick up ambient energy and act as if it were powered. One can, as indicated above, cycle just the power, but this may be less preferred in certain cases due to the possibility of unwanted interactions among antennas. One could also have all of the antennas powered simultaneously and cycle the tuning, but this may be less preferred in certain cases due to the increased consumption of energy.

In another embodiment, one antenna, such as antenna 122, may emit a signal out-of-phase with respect to the signals from the other antennas 124 and 126 with the cycle of operation involving sequential emission of a signal out-of-phase by each individual antenna.

Yet another embodiment may involve the mechanical movement of a first antenna while one or more of the other antennas are stationary. This movement may be translational movement, rotational movement or any other suitable type of movement, or a combination thereof.

Figure 11:
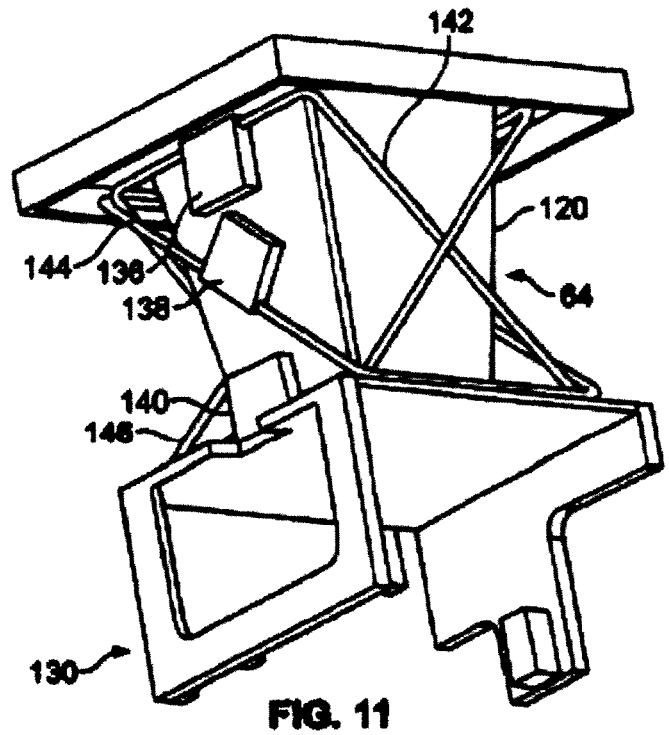
FIG. 11 is a perspective view partially broken away of an exit detection unit of the embodiment of FIGS. 1 through 8.
Figure 12:
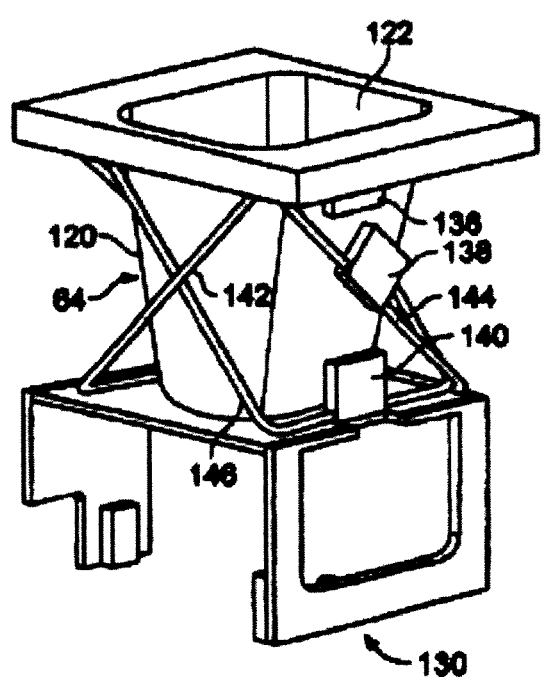
FIG. 12 is another perspective view of the exit detection unit of FIGS. 1 through 8.

Referring to FIGS. 11 and 12, with reference to the object exit detection zone 64 as shown in FIGS. 3 and 4, the structure has a housing 120 which may define an upwardly open recess 122 into which objects emerging from the surgical site may be introduced. Within the housing 120 (not shown) may be a receiving container for safely receiving and storing the used objects, which have passed through object exit detection zone 64, until safe disposal can be arranged. This container may be a suitably sized plastic bag having the desired strength. The housing 120, which, in the form shown tapers slightly downwardly, may have a closed bottom. Support frame 130 may serve as a support for the object exit detection zone 64.

Also shown in FIGS. 11 and 12 are antenna tuning circuits 136, 138 and 140, which may each be operatively associated respectively with a loop antenna 142, 144 and 146. The antennas may be of the same material and general configuration and relative orientation as the entry detection zone antennas. Loop antennas 142, 144 and 146 may be positioned at an angle to each other. This arrangement may facilitate the ability of the system to monitor and uniquely identify each object through its identifier, counting the exiting objects and identifying the type, regardless of relative orientation of the objects within recess 122 as the objects move downwardly through. The same general concepts described above in respect to the control of the antennas shown in FIGS. 9 and 10 may be employed in this context.

Figure 13A:
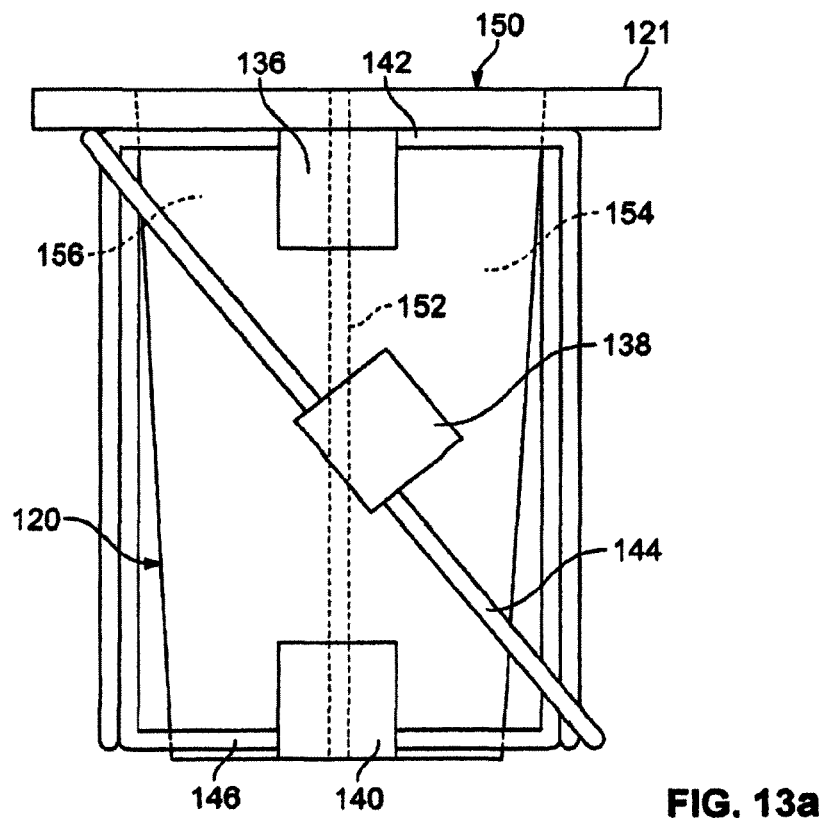
FIGS. 13a and 13b are respectively a schematic elevational illustration and a plan of single structure which functions as both an entry detection zone and an exit detection zone.
Figure 13B:
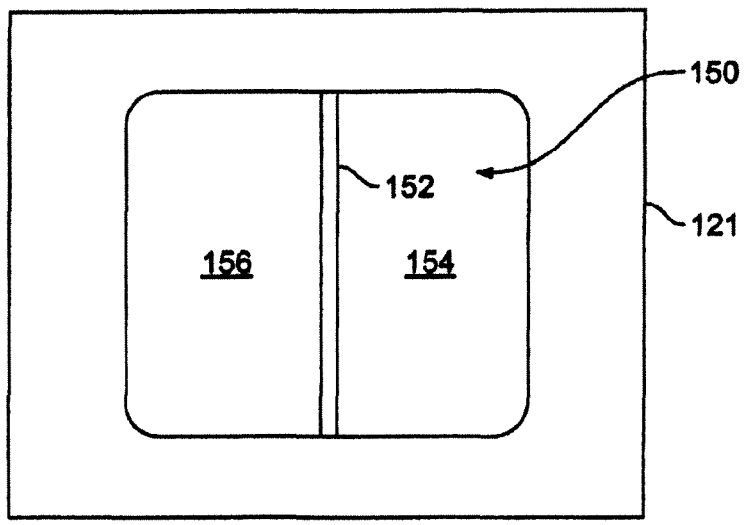

Referring to FIGS. 13a and 13b, another embodiment of the invention will be considered. In this embodiment, the construction of the device may be similar to the object exit detection zone shown and described in connection with FIGS. 11 and 12. In this embodiment, the tuning circuits 136, 138 and 140 may be operatively associated with their respective antennas 142, 144 and 146. Housing 120 may have an overlying cover 121 and may define a recess 150 which may have a divider wall 152 dividing the recess into compartments 154 and 156. Except for the dividing wall 152 dividing the recess 150 into compartments 154 and 156, the structural and functional arrangement may be similar or substantially identical to that shown and described in connection with FIGS. 11 and 12. In the present embodiment, however, a first compartment 154 may function as the object entry zone and the second compartment 156 may function as the object exit zone which would have a suitable container such as an appropriate bag (not shown) to collect the used and/or discarded objects.

Control circuitry 30 may be programmed in a manner known to those skilled in the art so as to determine whether it is functioning as an object entry zone or an object exit zone at a given time, to either scan in the objects entering or to scan out the objects exiting the surgical field. In one embodiment, a control circuitry 30 may rely on contextual data to determine if it is detecting a particular object or group of objects within a single package for the first time after control circuitry 30 is started up (e.g., scanning the objects into the surgical field) or the second time (e.g., scanning them out of the surgical field). An alternate approach may be to establish a flag in the object identifiers upon scanning them in order to confirm that unflagged objects are new and need to be scanned in. Upon exiting, the control circuitry 30 may determine the existence of previously flagged object identifiers which are being counted out. Control circuitry 30 may also be used to avoid re-using already-used objects. Control circuitry 30 may establish a flag with a certain value in the identifier of an object the first time it is scanned in the entry detection zone. If an identifier with a flag of that value is scanned, control circuitry 30 may warn the user that a used object is being be re-used, e.g., by a visual or auditory alert. Control circuitry 30 may also prevent the user from scanning subsequent objects when an identifier that has been flagged is scanned. The user may be equipped to over-ride control circuitry 30 when a warning is received and continue scanning. For example, the user may be provided with a pre-determined code that the user can enter into control circuitry 30 to continue scanning. The user may also be given an Override card which may be pre-programmed using RFID. If necessary, the user may scan the Override card at the appropriate scanner in order to continue scanning an object or to end the current scan and start the next one.

In another embodiment, control circuitry 30 may be adapted to maintain object counts and identities even when objects are introduced into the exit detection zone before they are introduced into the entry detection zone. For example, control circuitry 30 may be programmed to compare the list of identifiers detected in the exit detection zone with the list of identifiers detected in the entry detection zone. If an identifier is found on the list of identifiers detected in the exit detection zone but not on the list of identifiers detected in the entry detection zone, the identifier may be added to the list of identifiers detected in the entry detection zone. Alternatively, the user may be allowed to program control circuitry 30 to scan in objects in the exit detection zone without scanning them in the entry detection zone. This may be desirable, for example, in the case of an emergency when the user does not have time to scan objects in the entry detection zone before using them. The system may also be set up to maintain a count of the objects in a given package that have been scanned in the exit detection zone without being scanned in the entry detection zone, and to notify the user of the number of remaining objects in the package.

In yet another embodiment, control circuitry 30 may establish different types of flags in the object identifiers. For example, if it is required that an object that has been used in a surgical procedure be sanitized and reused, the control circuitry may establish a new type of flag in the object's identifier each time the object is scanned at the entry detection zone. The control circuitry may also store information about the object and the times it re-entered the entry detection zone. After a surgical procedure, the control circuitry may be consulted to get information about the frequency and timing of use of certain objects.

Among the additional features which may advantageously be provided through the control circuitry 30 are various alarm and warning systems. In one embodiment, the control circuitry may be programmed to compare the count and identity of objects processed by the entry scanner with objects processed by the exit scanner. The control circuitry may confirm that all objects entering said surgical field have been removed from the surgical field and may initiate an alarm in the event that, at the end of a surgical procedure, comparison of the data from the entry scanner with the data from the exit scanner indicates that not all the objects entering the surgical field have exited the surgical field. Control circuitry 30 may also stop the scanning of subsequent objects if comparison of the data from the entry scanner with the data from the exit scanner indicates that not all the objects entering the surgical field have exited the surgical field. The user may be equipped to over-ride control circuitry 30 when a warning is receive. For example, the user may be provided with a pre-determined code that the user can enter into control circuitry 30 to continue scanning. The user may also be given an Override card which may be pre-programmed using RFID. If necessary, the user may scan the Override card at the appropriate scanner in order to continue scanning.

In another embodiment, the device may warn the user to change the bag or container within the object exit detection zone 64 when the container is getting full of used objects. It may also provide a warning if a package of objects does not contain the proper number or kind of objects or if an identifier is not functioning properly on the scan in the object entry detection zone 62. In another embodiment, the bag or container may include an identifier. Control circuitry 30 may warn the user and/or stop functioning if the exit detection zone antennas do not detect the identifier of the bag. This ensures safer use of the device. Moreover, the control circuitry may be programmed to issue an alarm if there is an effort to scan the same object or package of objects into the object input inspection zone twice. In a manner known to those skilled in the art, the alarm may take the form of an audio alert or alarm, a visual alert or alarm, any other suitable alert or alarm or a combination thereof. The control circuitry may for example provide the visual alarm on the display screen.

Figure 15:
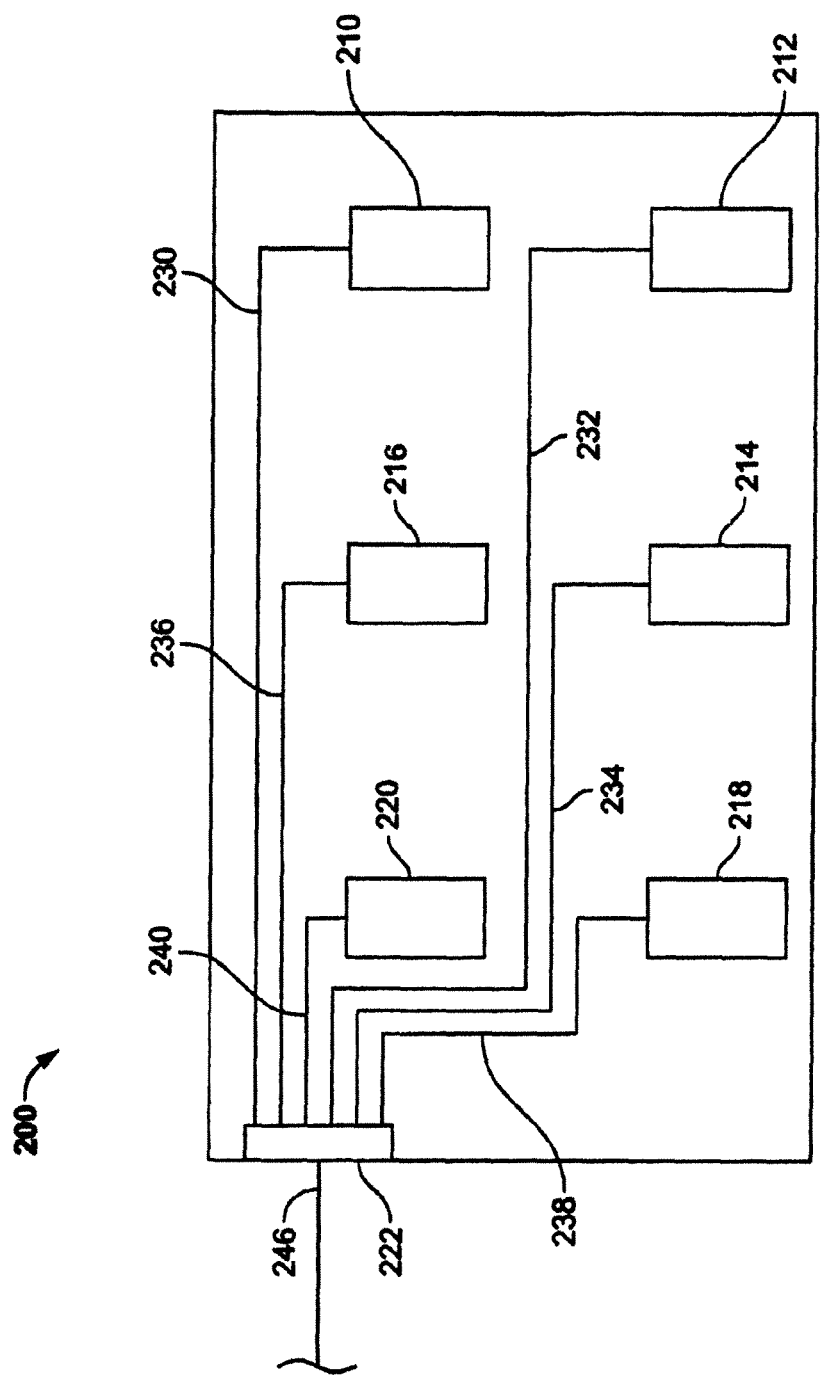
FIG. 15 is a schematic illustration of the positioning within a housing of a plurality of antennas for the embodiment of FIG. 17.

Referring to FIGS. 14 and 15, there is shown a surgical table which may have a suitable base 180, a support column 182 disposed in underlying supporting relationship with a horizontally extending patient support 184 over which a series of cushioned patient supports 190, 192 and 194 may be provided. During surgery, the supports 190, 192 and 194 may be covered by an appropriate sterile drape with the patient placed in position overlying the same. The support 184 may have a transverse recess within which may be inserted a housing 200 of the present invention containing a single antenna or an array of antennas structured to generate an upwardly directed detection field. A number of antennas, such as for example, between 2 and 6 or more, may be employed, as desired.

As shown in the schematic drawing of FIG. 15, the housing 200 in the form shown may contain a plurality of antennas 210, 212, 214, 216, 218 and 220, each of which may be connected to electrical connector 222 by respective wires 230, 232, 234, 236, 238 and 240. The wires 230, 232, 234, 236, 238 and 240 may in turn emerge from the housing 200 as shown in FIGS. 14 and 15 to an electrically conductive wire 246. Wire 246 may be connected to control circuitry 250 which may serve the multipurpose of supplying power to and controlling operation of the antennas 210, 212, 214, 216, 218 and 220, as well as receiving data returned from the identifiers on objects in the surgical site or adjacent thereto. The control circuitry 250 may also control the time and content of the detection fields being generated by the antennas by providing power to each one in sequence, by tuning and detuning the same to a specific desired resonant frequency or by controlling the signals emitted by the same to create an out-of-phase relationship. In the form shown, the housing 200 may be inserted completely into the horizontal support 184. The housing 200 may then underlie the surgical site so as to generate a detection field within the patient and surgical site to obtain data on whether any object is in the patient or has been left in the patient at a time approaching closing the patient after surgery. The system may also be employed, if desired, to determine what objects are in a patient or, more generally, are in the surgical field, and at what location immediately prior to, during and after a surgical procedure. Additionally, information about the amount of blood and fluid loss may be obtained, as previously discussed.

A support post 260 may have a floor-supported base 247 which may serve to support the control circuitry 250 and a visual display unit 264 may be positioned at a higher elevation than the control circuitry 250 and may be secured to support post 260 by clamp 261. This may provide ready visual access to the visual display window 266. Suitable control buttons such as 265, 267, 268 and 269 may be provided on the visual display unit 264 to provide a display of the desired information.

Referring to FIG. 14, in addition to or instead of the underlying lower array of antennas 210, 212, 214, 216, 218 and 220 contained within housing 236, the invention may include the use of a handheld antenna 270 which may be contained within a handheld wand 272. The handheld wand 272 may be electrically energized by wire 278 and may also serve to communicate data to and from the control circuitry 250. In the alternative, the antenna 270 may be unpowered. If desired, a plurality of antennas may be employed in the handheld wand 272. This overlying handheld wand 272 may be moved around the patient and/or the surgical field so as to cooperate with the underlying antenna-containing housing 200 in order to define a section field.

In one embodiment, lower antennas 210, 212, 214, 216, 218 and 220 may be electromagnetically coupled with handheld antenna 270 in order to increase the reading range of the lower antennas. Lower antennas 210, 212, 214, 216, 218 and 220 may also vary the direction of the detection field created by handheld antenna 270 as it is moved across the patient in a manner such that the resulting magnetic field contains vector components of more varied direction than if handheld antenna 270 were used alone. This may increase the likelihood of activating and reading identifiers positioned in arbitrary orientations within a patient's body.

Figure 16A:
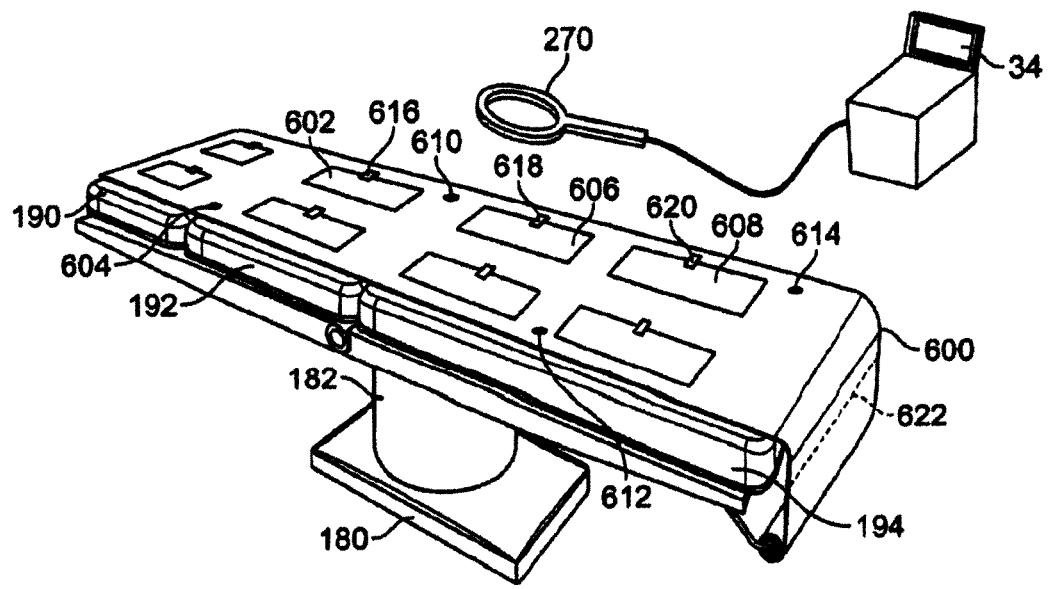
FIGS. 16a and 16b show a mat of one embodiment of the invention.
Figure 16B:
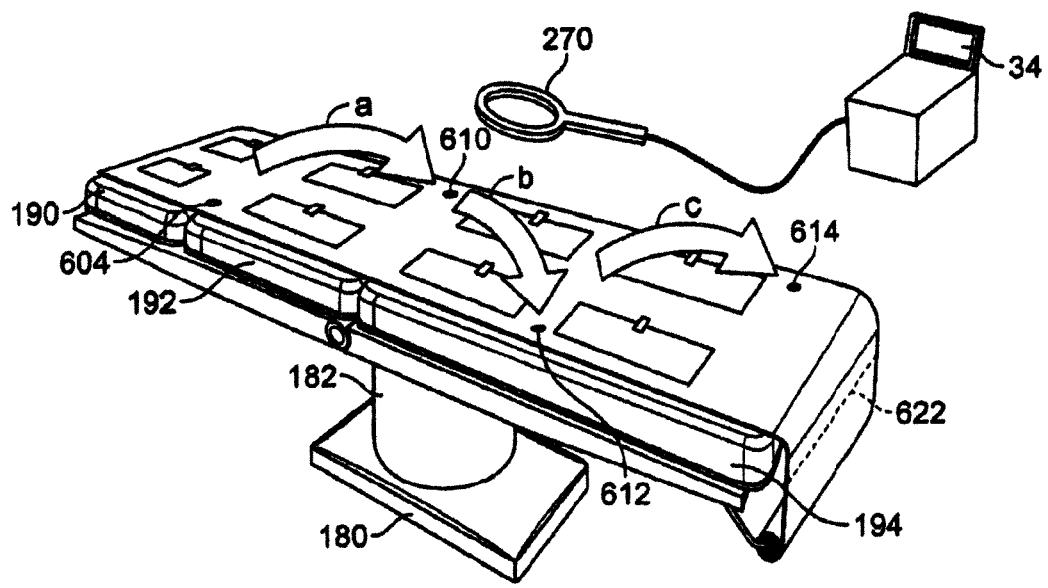

In another embodiment, lower antennas 210, 212, 214, 216, 218 and 220 may be embedded or otherwise attached to a mat that may be placed on top of the surgical table and under the patient. It may then take the form of a mat, which may be reusable or disposable. Having a disposable mat may be desirable for example, in a surgical procedure where any item placed under a patient may become soiled. The mat may be made of one or more different materials and may be of different shapes and/or dimensions. In one embodiment, the mat may be a modified surgical table drape. The mat may also contain identifiers which may be detected by handheld antenna 270. Identifiers of the mat may also be inspected by the entry detection zone, the exit detection zone, or both (e.g. by folding the mat so that it fits within the zone or by using a flat entry or exit detection zone, as illustrated in FIG. 5). A plurality of identifiers may be encoded with specific information indicating their location relative to the other identifiers in the mat. The identifiers may be positioned at various locations in the mat and control circuitry 30 may instruct the user to scan the identifiers in the mat in a specific order. This may ensure that the user scans the entire body of the patient when scanning with handheld wand 272. This may in turn ensure an accurate detection of all the objects within the patient's body. For example, FIG. 16*a* shows a mat according to one embodiment of the invention. Mat 600 may have antennas, such as antennas 602, 606 and 608 embedded in it which may be used to read information from identifiers on objects in the surgical field. Antennas 602, 606 and 608 may each include a loop of circuit trace made of any suitable conductive material and a tuning circuit (e.g. tuning circuits 616, 618 and 620 respectively). Mat 600 may also have one or more identifiers, such as identifiers 604, 610, 612 and 614 which may be detected by handheld antenna 270 in order to ensure that the entire surgical site is scanned. Mat 600 may include perforation 622, along which mat 600 may be torn after a surgical procedure for ease of disposal. Mat 600 may also be in the form of a continuous roll, allowing the user to pull and tear off a section along perforation 622 as desired. As shown in FIG. 16*b*, visual display 34 may instruct the user to scan identifiers 604, 610, 612 and 614 in mat 600 in a specific order. Arrows a, b and c may show the order in which identifiers 604, 610, 612 and 614 may be scanned. In this example, the order of scanning may be identifier 604, identifier 610, identifier 612 and lastly, identifier 614. Visual display 34 may display information relating to objects (e.g. the number and identity of the objects it detects) as well as information regarding handheld antenna 270 (e.g. whether or not handheld antenna 270 is within reading range of mat 600). Control circuitry 30 (FIG. 1) may, for example, determine whether handheld antenna 270 is in range by determining whether handheld antenna 270 can read identifiers 604, 610 612 and 614 in mat 600. If handheld antenna 270 is not within reading range of identifiers 604, 610, 612 and 614 in mat 600, a warning may be issued using any appropriate method, and the user may be asked to adjust the location of the handheld antenna to achieve proper reading range.

The identifiers in the mat may also be used to ensure that a new mat is used for each surgical procedure. In one embodiment, the mat may be scanned at the beginning of a surgical procedure with the antennas in object entry detection zone 16 or with handheld antenna 270. A flag may be established in each identifier in the mat that is scanned in. For example, each identifier that is scanned in at the beginning of a surgical procedure may have a flag set to "true." Control circuitry 30 may then be set up to detect any identifier that has a flag set to "true" and to alert the user that the mat being scanned may be used. This may prevent a mat from being used in more than one surgery. Control circuitry 30 may also be set up to prevent subsequent scanning of identifiers when it detects an identifier that has a flag indicating that it has already been scanned (e.g. at the beginning of a surgical procedure). The user may be equipped to over-ride control circuitry 30 when control circuitry 30 prevents the scanning of identifiers. For example, the user may be provided with a pre-determined code that the user can enter into control circuitry 30 to continue scanning. The user may also be given an Override card which may be pre-programmed using RFID. If necessary, the user may scan the Override card at the appropriate scanner in order to continue scanning.

The handheld antenna 270, which may be disposed within the handheld wand 272, may be employed to act as an entry or exit antenna thereby providing added data from objects that are scanned in and out of the surgical field with an additional reading in respect of the surgical site. There are several ways in which this may be accomplished. The handheld antenna 270 may operate in a default mode such that it scans objects which are being taken out of the surgical site. It may also be employed in a contextual manner so that the first time it sees a specific identifier on a specific object, it is regarded as entering the surgical site while the second time it sees it, it is regarded as exiting the surgical site. There may also be an additional user control in the form of a switch, such as a toggle switch (not shown), on the handle of the handheld antenna 272 for the user to determine whether items are being scanned in or out.

In one embodiment, handheld wand 272 may not be attached to support post 260 by wire 278 and may powered for example by using batteries. In this embodiment, handheld wand 272 may be moved over a range of distances within the surgical field. Handheld antenna 270 may as a result have a wider reading range and may be able to produce a detection field with a greater range of directionality. Handheld wand 272 may also contain an identifier (not shown). Lower antennas 210, 212, 214, 216, 218 and 220 may be used to detect the identifier in handheld wand 272 when handheld wand 272 is at different locations from the surgical site. This may ensure that the reading range of handheld wand 272 is confirmed before it is used to detect identifiers that may be in the body of a patient. The visual display unit 264 may also be employed to present data from the handheld wand 272.

If desired, the antenna containing housing 200 may be permanently or removeably secured to the surgical table or the antennas could otherwise be permanently or removeably secured to the table.

If desired, the handheld unit may also be employed with other embodiments in the invention, including but not limited to those described in the context of FIGS. 1-12.

Figure 17:
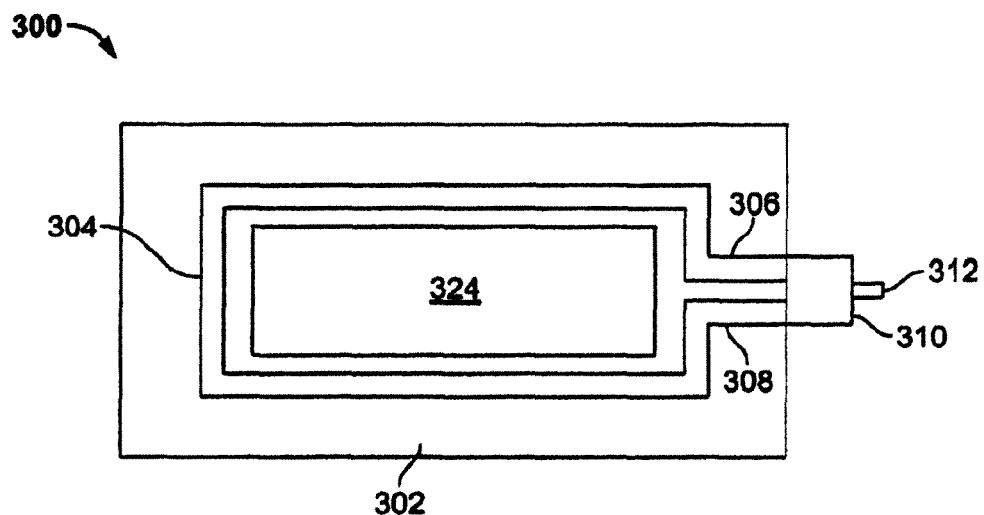
FIG. 17 shows a top plan view of another embodiment wherein an antenna is provided on an adhesively backed member which may be secured directly to the patient.
Figure 18:
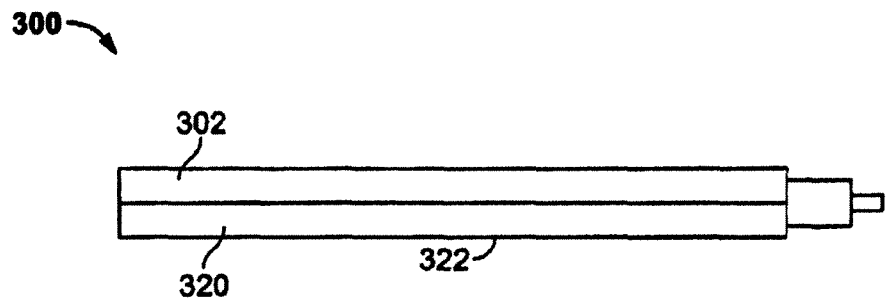
FIG. 18 is a side elevational view of the embodiment shown in FIG. 17.

FIGS. 17 and 18 show another embodiment wherein an antenna assembly 300 may have an upper layer 302 on which is secured an antenna 304. Antenna 304, in the form shown, may be a rectangular loop having a pair of free ends 306 and 308. Free ends 306 and 308 may be secured to a connector 310 which may have an electrically conductive element 312 which may be structured to transmit data to and from the control circuitry (not shown) and, if the antenna 304 is to be powered, to energize the same. In the form shown, the antenna 304 may be of metal tubular configuration. The antenna 304 may be secured to an underlying layer 320 which may have an undersurface provided with a pressure-sensitive adhesive 322. An opening 324 may permit the antenna to be secured around the site of the surgical incision (not shown). It will be appreciated that the opening 324 and antenna size and configuration may be provided in a number of sizes and shapes in order to accommodate different surgical procedures and incision sizes.

Antenna 304 may be powered, or it may be unpowered and have the pad 302 powered. If the antenna 304 is unpowered, the antenna may be connected to the control circuitry (not shown in this view) and report back its data or may be completely unconnected and simply act as a guide to direct, define or extend the range of field from other antennas. In this form, the antenna may be provided as a disposable item. In a further embodiment, the construction of FIGS. 17 and 18 may combine the above-described antenna with an electrocautery grounding pad in order to permit an electrocautery machine to function.

Figure 19:
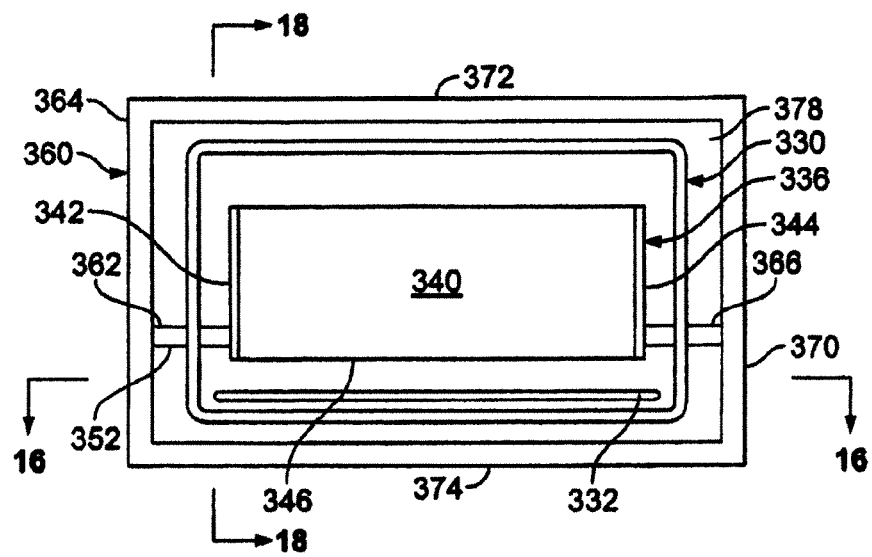
FIG. 19 shows a schematic front elevational view of a modified form of the object detecting apparatus of the present invention.

Referring now to FIGS. 19 through 22, a further embodiment of the invention will be considered. In this embodiment, in the form shown, a pair of closed-loop antennas 330 and 332 may be made of a tubular electrically conductive material such as copper, and may be at an angle to each other. In the form shown, vertically oriented antenna 330 may be disposed about 40% to about 60% of the distance D between the front portion of generally horizontal antenna 332 and the rear portion thereof. A rotatable object receiver 336 may have a rear wall 340, a pair of spaced walls 342 and 344 and a base wall 346 which may cooperate to define a object-receiving recess 356. As shown in FIG. 19, the rotatable object receiver 336 may have a support rod 352 which may have opposed ends secured within housing 360 with a first end 362 being received within housing wall 364 and a second end 366 being received within housing wall 370. The housing may have an upper wall 372, a lower wall 374 which may have an opening 376 to permit objects to be withdrawn therethrough and a rear wall 378.

Elongated rod 364 may either be fixedly secured to the housing 360 with the object receiver 336 being rotatable with respect thereto or, in the alternative, the object receiver 336 may be fixedly secured to elongated rod 364 which may have its ends 362 and 366 rotatably secured within housing walls 364 and 370.

Figure 20:
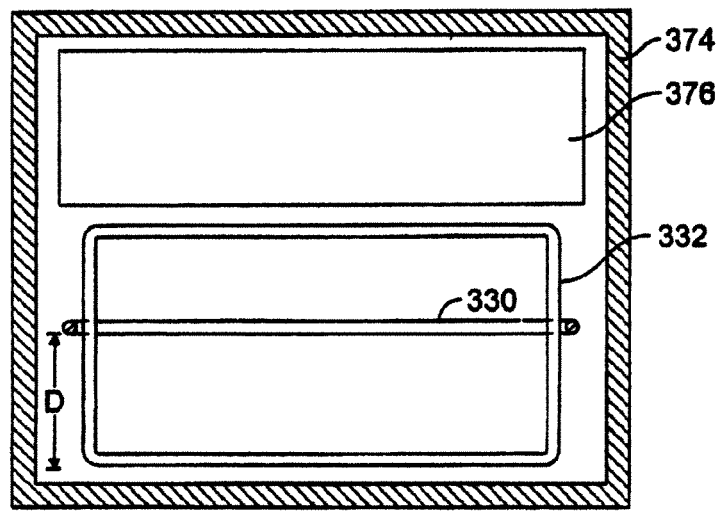
FIG. 20 is a cross-sectional illustration of the object detecting apparatus of FIG. 19 taken through 16-16.
Figure 21:
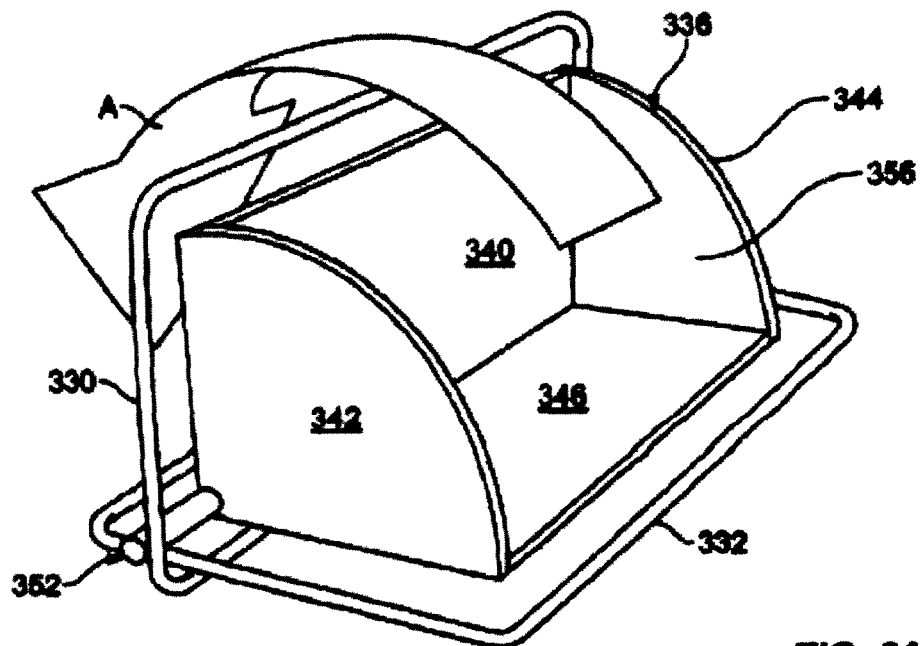
FIG. 21 is a schematic illustration showing the object receiver and its relative movement with respect to a pair of fixed antennas.
Figure 22:
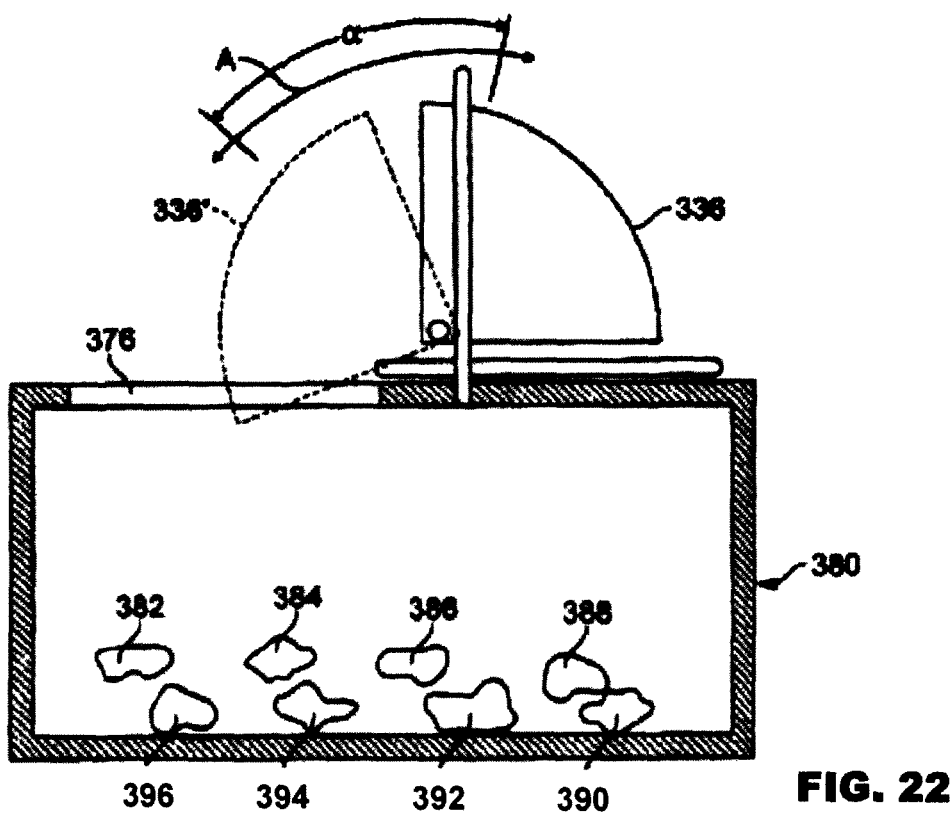
FIG. 22 is a cross-sectional illustration taken through FIG. 19 at 18-18.
Figure 23:
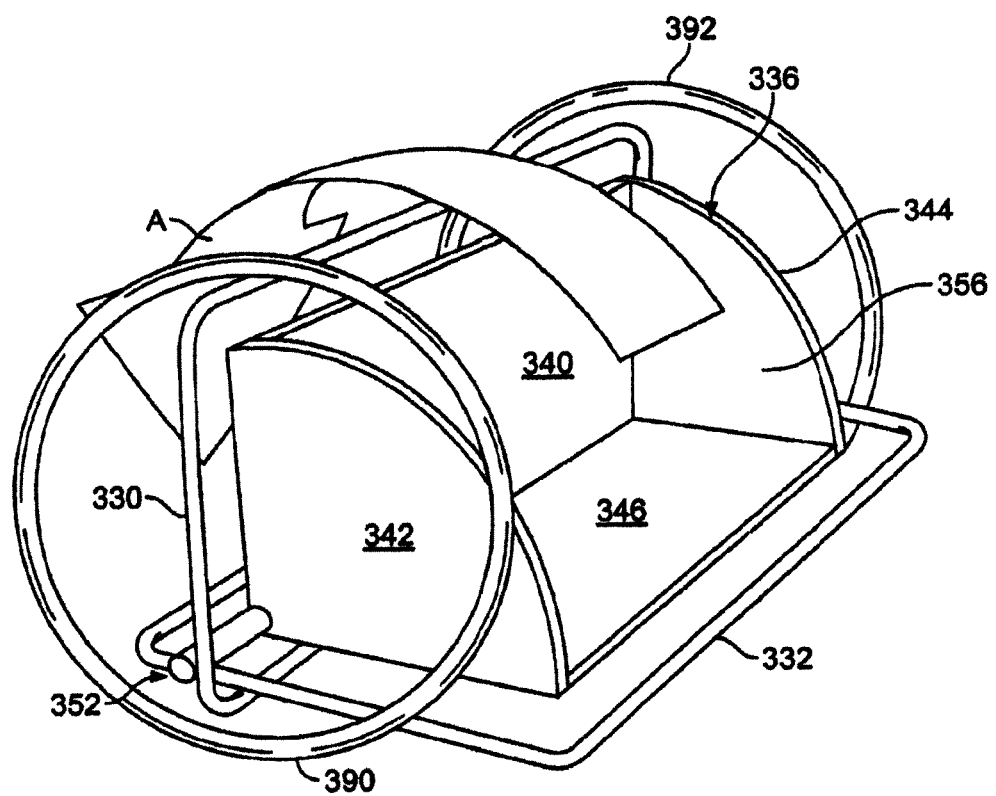
FIG. 23 shows a modified version of the object detecting apparatus of FIGS. 19 through 22.

In FIG. 22 reference number 336 shows the object receiver 336 in the forward position while reference number 33e shows the object receiver 336 in the rearward position. The object receiver 336 may rotate in the direction indicated by two-headed arrow A. As shown in FIG. 20, the base wall 374 of housing 360 has an opening 376 through which objects may be discharged into a container 380 when the receiver is rotated rearwardly. It will be preferred that the angle .alpha. embraced by the forwardmost position of object receiver 336 and rearwardmost position 336.sup.1 be such that in the forwardmost position, one or more objects may be introduced easily into the object receiver 336, while in the rearmost position, the object or objects will readily drop under the influence of gravity into underlying container 380 (FIG. 22). The angle .alpha. between the forwardmost position and rearwardmost position may be about 40.degree. to about 90.degree.

In FIG. 22, there is shown a number of objects 382, 384, 386, 388, 390, 392, 394 and 396 which have been delivered into receiver 336 and deposited into the container 380. In this form, the rotatable receiver 336 has been used in the object exit detection zone. When used in the exit mode, it will be appreciated that the housing 360 and the receiver 336, as well as the antennas contained therein, may be positioned over the desired collection container 380 which may have different sizes and shapes, if desired. This embodiment may also be employed in the object entry zone with delivery of the object to an individual who would remove it from the object receiver 336.

The embodiment of FIGS. 19 through 22 may be employed with a plurality of objects being processed simultaneously. The system, in respect of control circuitry interaction, could function in the above-described manner.

Figure 26:
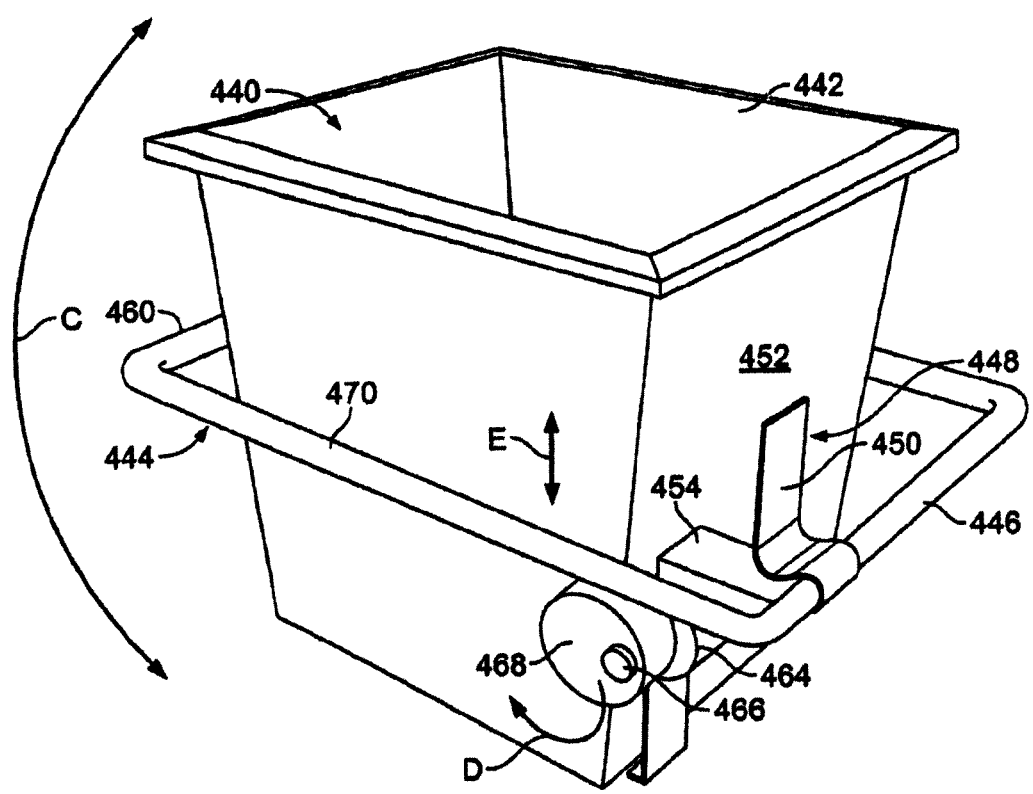
FIG. 26 illustrates another embodiment of the invention providing for establishing movement between an antenna and the object-receiving recess of the scanner.

Referring to FIG. 26, a refinement of the embodiment of FIGS. 19 through 22 is shown. In this embodiment, a pair of side antennas 390 and 392 may be disposed on opposite sides of antennas 330 and 332 oriented at an angle to each other. This may facilitate reading object identifiers in a third dimension. These antennas 390 and 392 are oriented generally parallel with respect to each other. While in the form shown, the antennas 390 and 392 are of generally circular configuration, other configurations may be employed, if desired.

Figure 24:
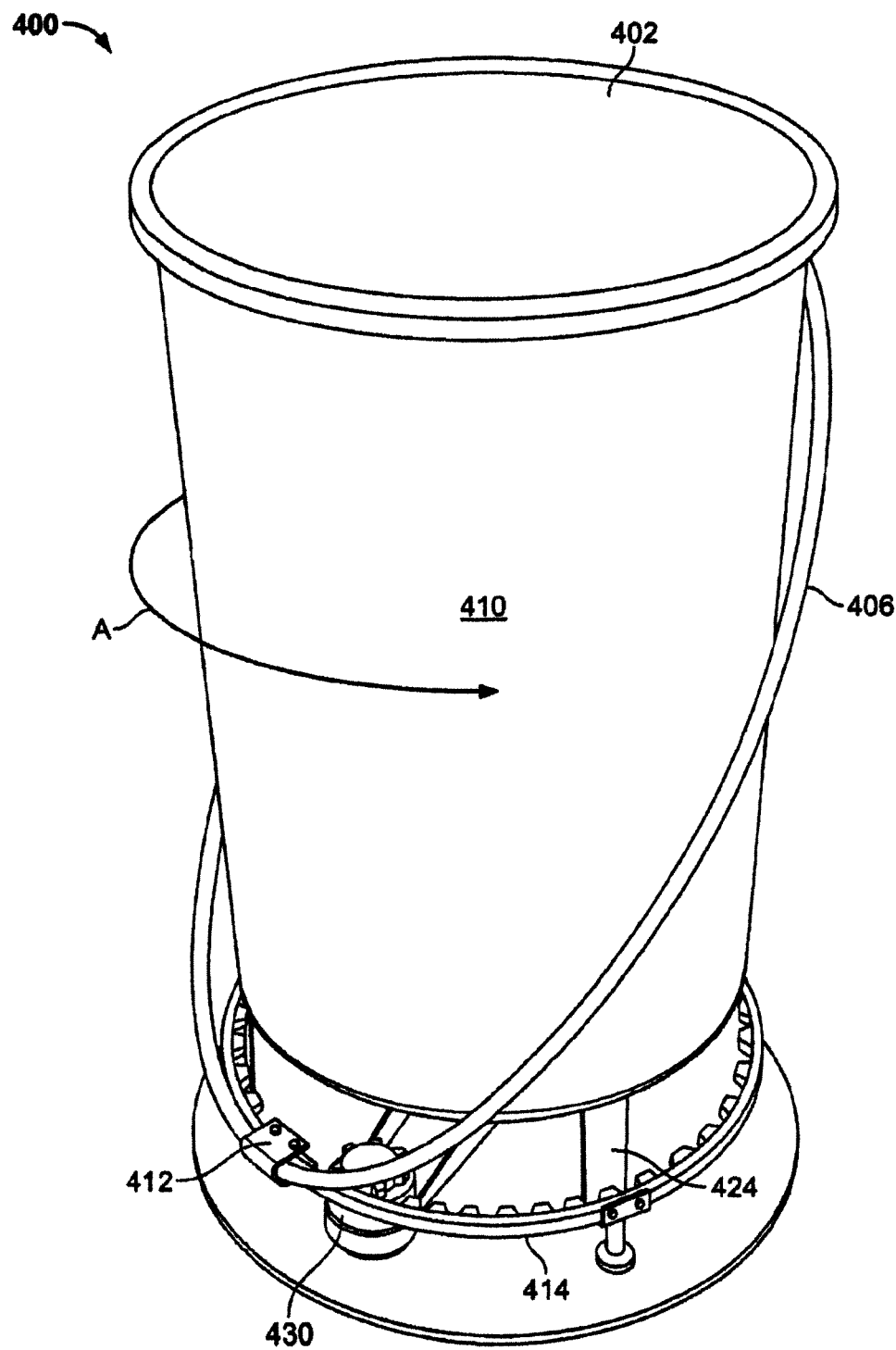
FIG. 24 is a perspective view of a form of scanner having the capability for effecting movement of an antenna with respect to the object-receiving portion of the scanner.
Figure 25:
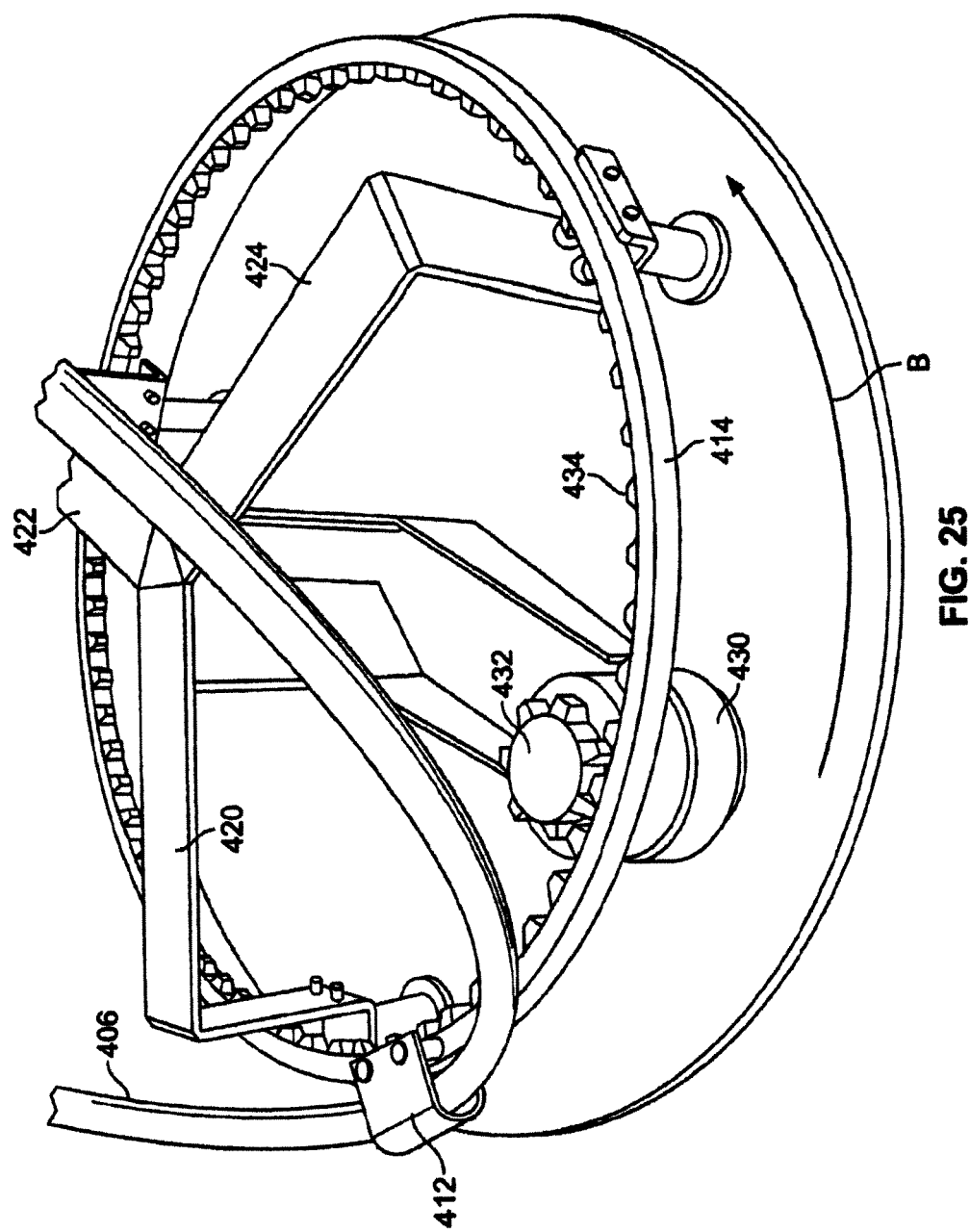
FIG. 25 is a fragmentary detailed view of a portion of the scanner of FIG. 24.

Referring to FIGS. 24 and 25, there is shown a scanner housing 400 which may define an upwardly open object-receiving recess 402. A closed-loop antenna 406 may be oriented generally angularly upwardly and around the exterior surface 410 of the scanner 400. In this embodiment, the antenna 406 may be fixedly secured by a suitable clamp 412 to a rotatable ring 414 which, through support members, such as arms 420, 422 and 424, may be fixedly secured to the undersurface of the scanner 400 such that rotation of the ring 414 will effect rotation of the antenna 406 about the scanner 400. A motor 430 may have an output shaft secured to pinion 432 which may be engaged with annular rack 434. It will be appreciated that in this manner when a motor 430 is energized, the ring 414 will rotate in direction indicated by arrow B with respect to the scanner 400, thereby establishing relative movement between the objects contained within recess 402 and the antenna 406. This facilitates obtaining the desired data with respect to the objects regardless of the orientation and depth of the objects within the recess 404.

While the embodiment of FIGS. 24 and 25 has a object-receiving recess of substantial depth and is particularly suitable for use as an exit scanner, this embodiment may also be employed as an entry scanner. When employed as an entry scanner, a more shallow receptacle is preferably employed.

Referring to FIG. 26, there is shown a scanner having a housing 440 which defines an upwardly open object-receiving recess 442. A generally loop-shaped antenna 444 may have an end segment 446 within a strap element 448 which has one portion 450 fixedly secured to outer surface 452 of the scanner container 440 and another portion 454 secured to another portion of the outer surface 452. The strap element 448 may define a loop wherein tubular section 446 is rotatably mounted. The loop-shaped antenna 444 may be disposed exterritoriaIy of and spaced from the scanner housing 440. When the antenna 444 is rotated in a manner to be described hereinafter, end 460 of the antenna may move generally up and down, generally in the direction indicated by arrow C. A motor 464 has its output shaft 466 eccentrically mounted within cam member 468 such that energizing the motor 464 will cause rotation of the eccentric cam 468 in the direction of arrow D which will create responsive reciprocating generally upward and downward movement of section 470 of the antenna as indicated generally by the double-headed arrow E. In this manner, relative movement between the antenna 444 and the objects contained within recess 442 will be mechanically achieved.

Figure 27:
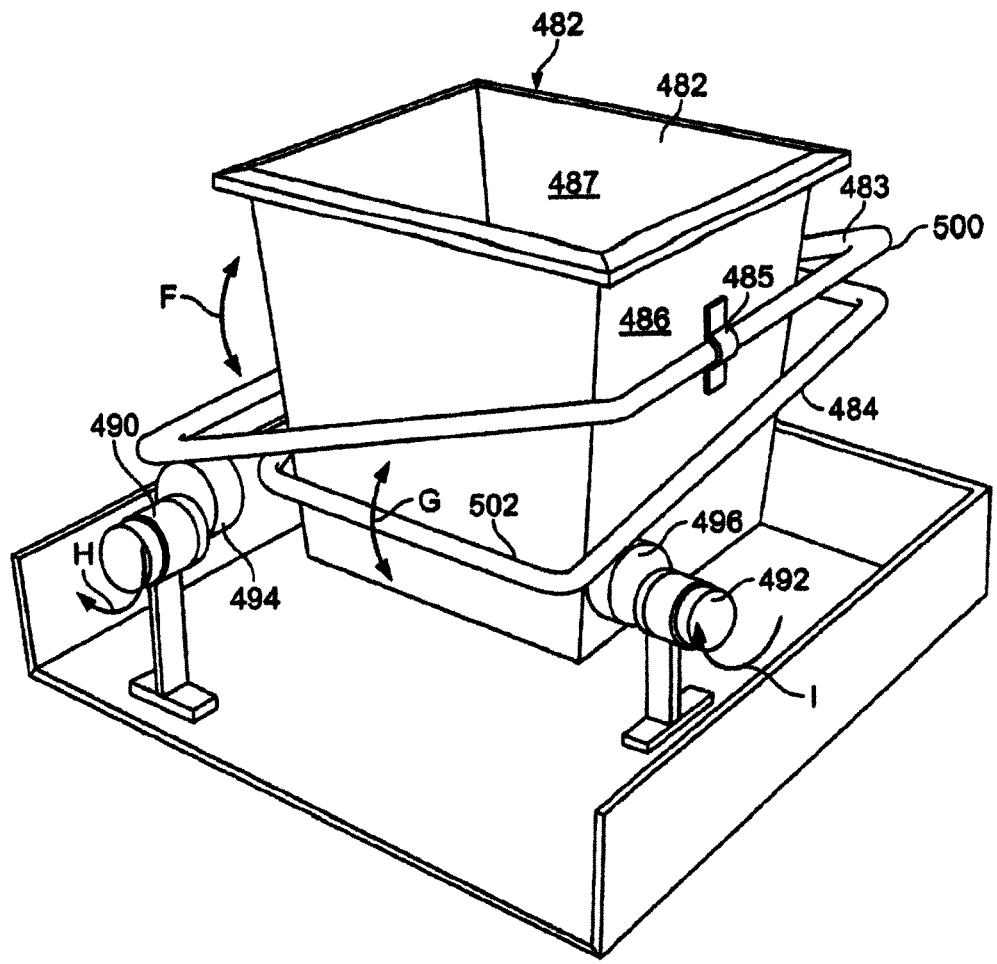
FIG. 27 is a perspective view showing a pair of antennas which may be subject to relative movement with respect to the scanner object-receiving recess.

Referring to FIG. 27, there is shown a scanner container 480 which defines an upwardly open object-receiving recess 482, a pair of loop-shaped antennas 483 and 484 which are structured to be rotated respectively in the directions indicated by arrows F, G (section 502) responsive to motors 490 and 492 effecting rotation of their respective cam elements 494 and 496 in the direction indicated respectively by arrows H and I. The antennas 483 and 484 are oriented to rotate generally in planes perpendicular to each other. Antenna 483 may have section 500 rotatably mounted to the exterior of wall 486, such as in the manner in which antenna 444 is mounted in FIG. 26, for example, by strap 485. Antenna 484 may similarly be rotatably secured to the exterior of wall 487.

Figure 28:
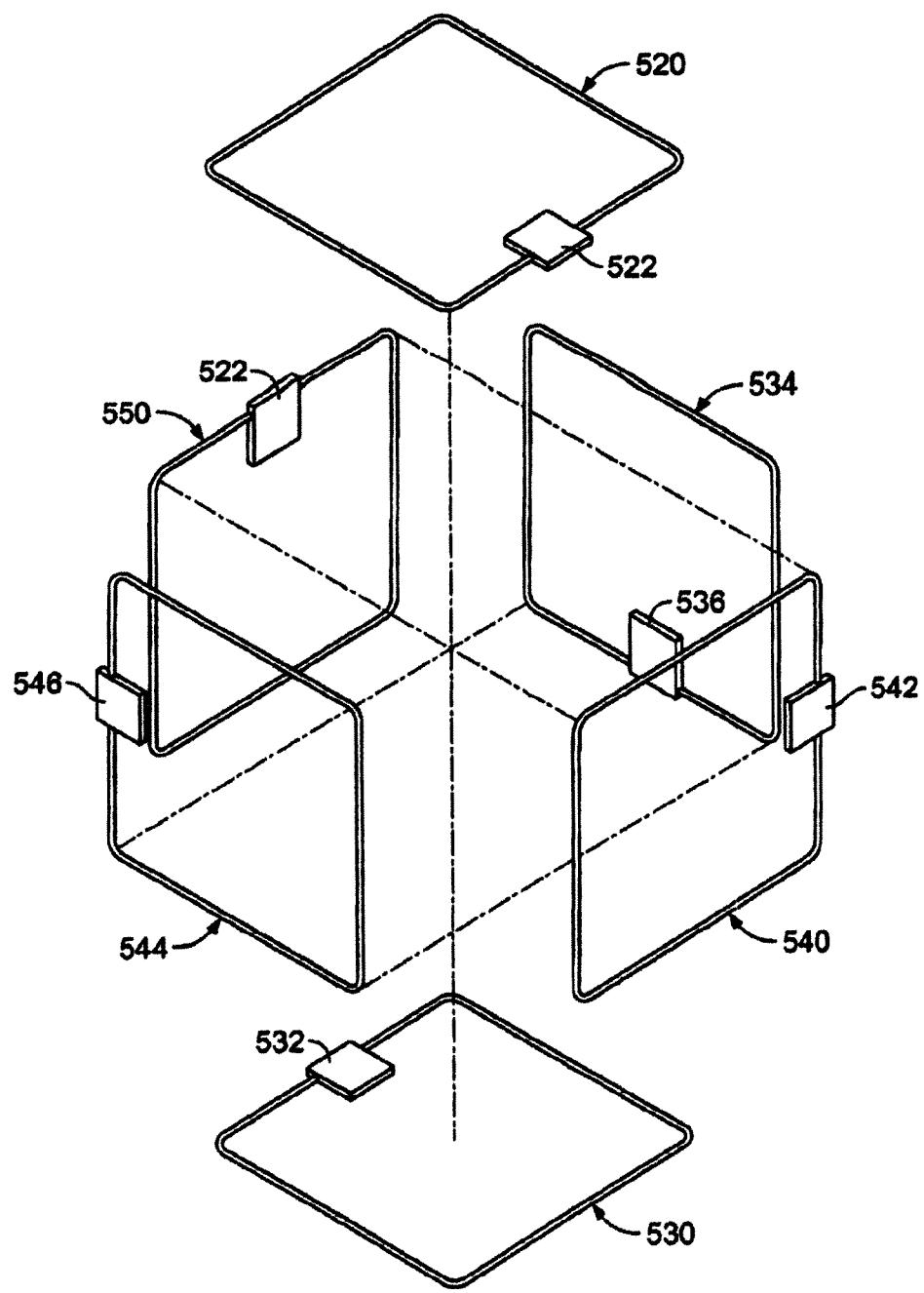
FIG. 28 has an exploded view of six generally square closed-loop antennas and associated tuning circuits which, when assembled, may function in a scanner of the present invention.
Figure 29:
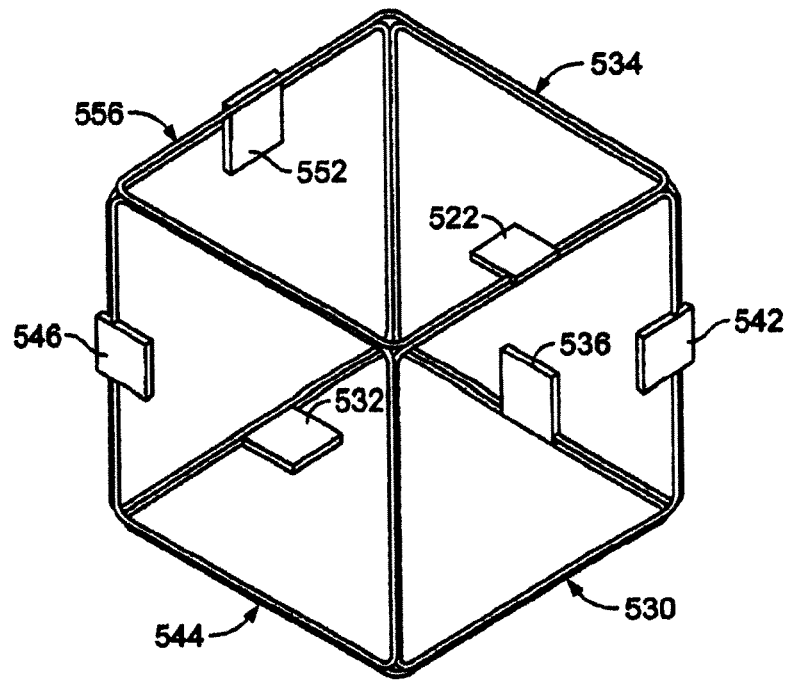
FIG. 29 is a perspective view of an assembly of antennas created from the individual antennas shown in FIG. 28.

Referring to FIGS. 28 and 29, three pairs of opposing antennas, each having their own tuning circuits, are assembled into a generally cube-like configuration. The antennas which are shown in the illustrations may be square-shaped looped antennas. A first pair of antennas 520, 530 may have, respectively, associated tuning circuits 522 and 532. A second pair of antennas 534 and 544 may have, respectively, associated tuning circuits 536 and 546. A third pair of antennas 540 and 550, respectively, may have associated tuning circuits 542 and 552.

In this embodiment of the invention, several methods of operation may be employed. For example, a pair of antennas, such as 520 and 530, may be powered, while the others are not powered, with a cycle of operation involving sequentially powering each of the three pairs of antennas during a time when the other two pairs are not powered. In another embodiment, a pair of antennas powered and tuned, while the others are powered and detuned. A similar cycle of operation may be employed. Each pair of antennas sequentially may be powered in phase or out of phase in order to direct the field, but it will generally be preferred to have the powering occur in phase so as to create a higher concentration of magnetic flux in the space between the pair of antennas and to eliminate radiation outside thereof. These embodiments may be controlled by the control circuitry (not shown in these views). In another embodiment, one of each pair of opposing antennas may be unpowered or may or may not have its tuning adjusted in concert with the opposing antenna of the pair.

Figure 30:
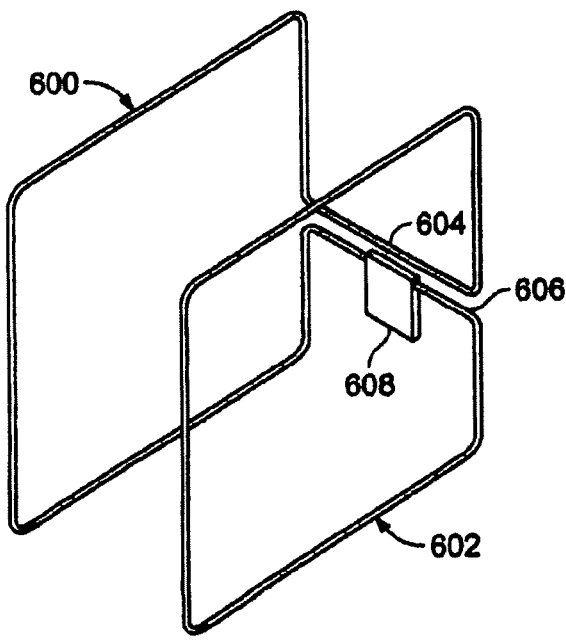
FIG. 30 is a partially schematic illustration of a single antenna with two opposing loops connected by a bridge along with its tuning circuit.

Referring to FIG. 30, there is shown a single antenna having two opposed loops 600 and 602 connected by a bridge 604 and 606 and having appropriate tuning circuitry 608, which is controlled by the control circuitry (not shown in this view). The antenna of FIG. 30 may be employed as a substitute for a pair of opposed antennas, such as those shown in FIGS. 28 and 29. This antenna creates the same gate effect as two opposing antennas powered and tuned simultaneously and in phase with one another. It will be appreciated that one or more of the antennas of FIG. 30 may be combined with opposing pairs of antennas.

Figure 31:
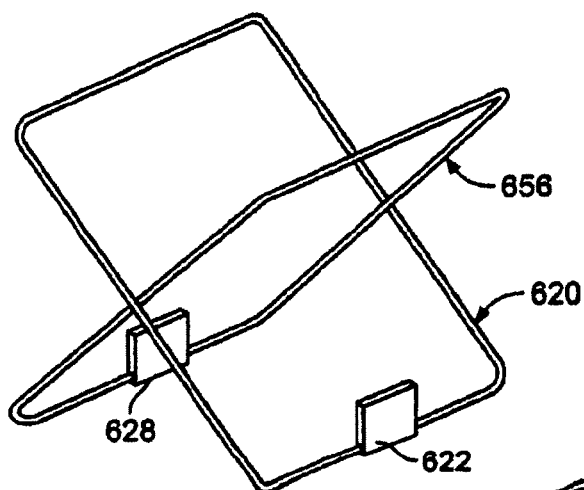
FIG. 31 shows a pair of looped antennas and their associated tuning circuits placed in relative position which enables them to create a rotating field.

Referring to FIG. 31, there is shown a further modification of the invention wherein a pair of closed-loop generally rectangular antennas 620 and 626, each having their respective turning circuits 622 and 628, are oriented generally perpendicular with respect to each other. This antenna pair may also substitute for a pair of antennas of FIGS. 28 and 29. The antenna pair of FIG. 31 may be powered and tuned simultaneously and be 180.degree. out of phase with one another. This structure creates a rotating field inside the boundary of the physical space. The field lines sweep 360.degree. through the plane which is mutually perpendicular to the plane of each antenna 620 and 626. The embodiment of FIG. 31 replaces two pairs of opposing antennas or two double loop antennas. It is preferred to minimally employ a set of opposing antennas or one double loop antenna in conjunction with the antenna pair of FIG. 31. The antennas 620 and 626 may be oriented such that their fields are directed at an angle to the rotating field created by these antennas.

Figure 32:
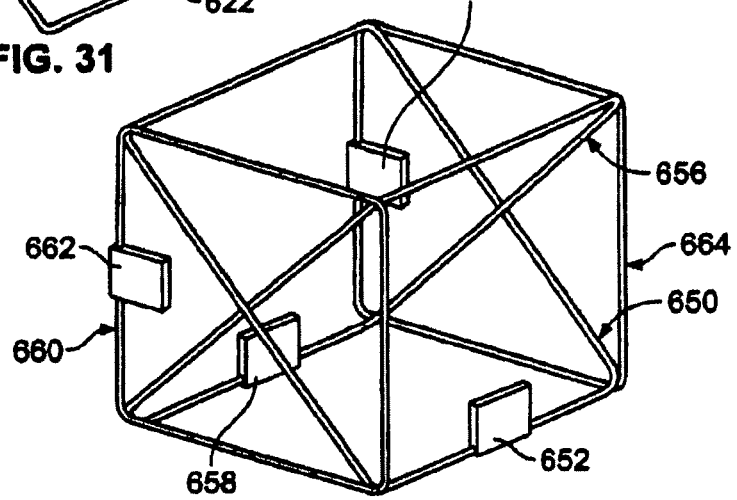
FIG. 32 is a perspective view of a pair of spaced, loop antennas combined with a pair of antennas configured as in FIG. 31.

FIG. 32 shows a pair of antennas 650 and 656 having associated respective tuning circuits 652 and 658 positioned between a pair of opposed loop antennas 660 and 664, each of which has its associated tuning circuit 662 and 666. The field generated by antennas 660 and 664 is at an angle to the rotating field created by antennas 650 and 656.

Figure 33:
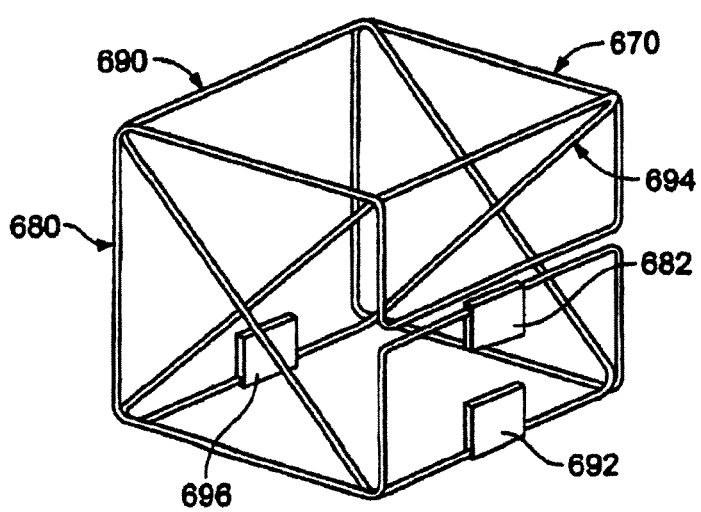
FIG. 33 is a perspective view of a group of antennas.
Figure 34:
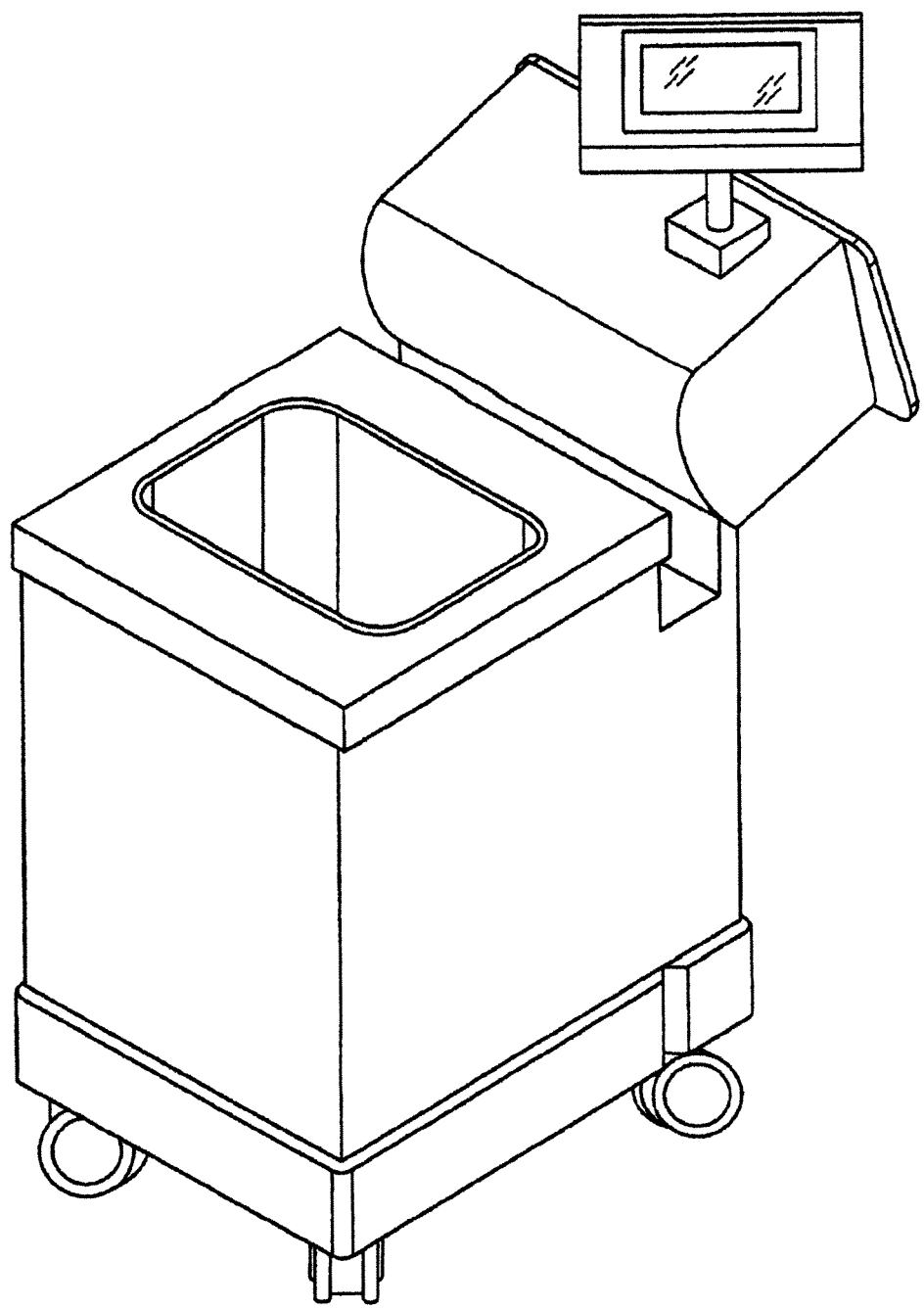
FIG. 34 is a perspective view of a form of system of one embodiment of the invention.
Figure 35:
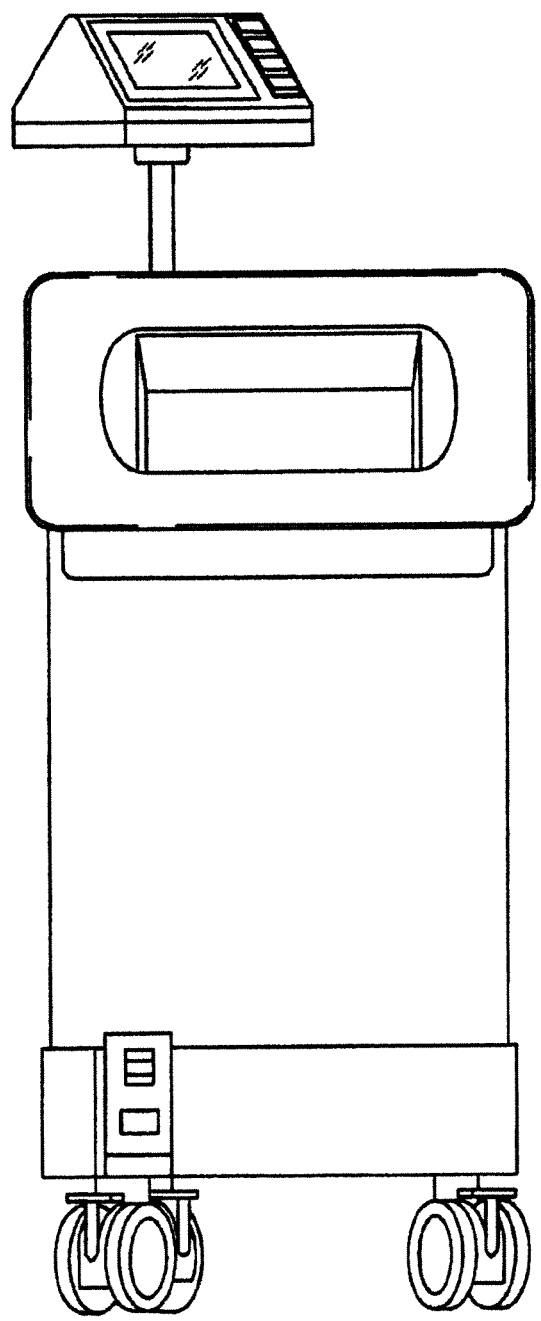
FIG. 35 is a front elevational view of the system illustrated in FIG. 34.
Figure 36:
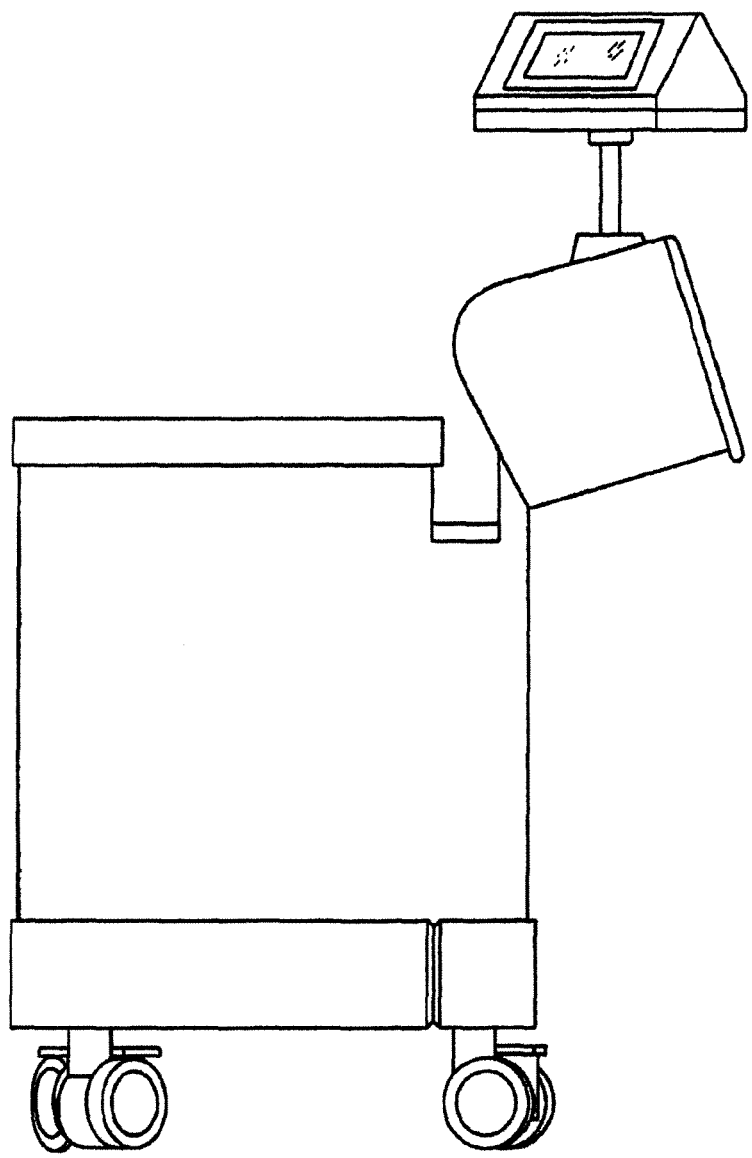
FIG. 36 is a left-side elevational view of the system shown in FIG. 34.
Figure 37:
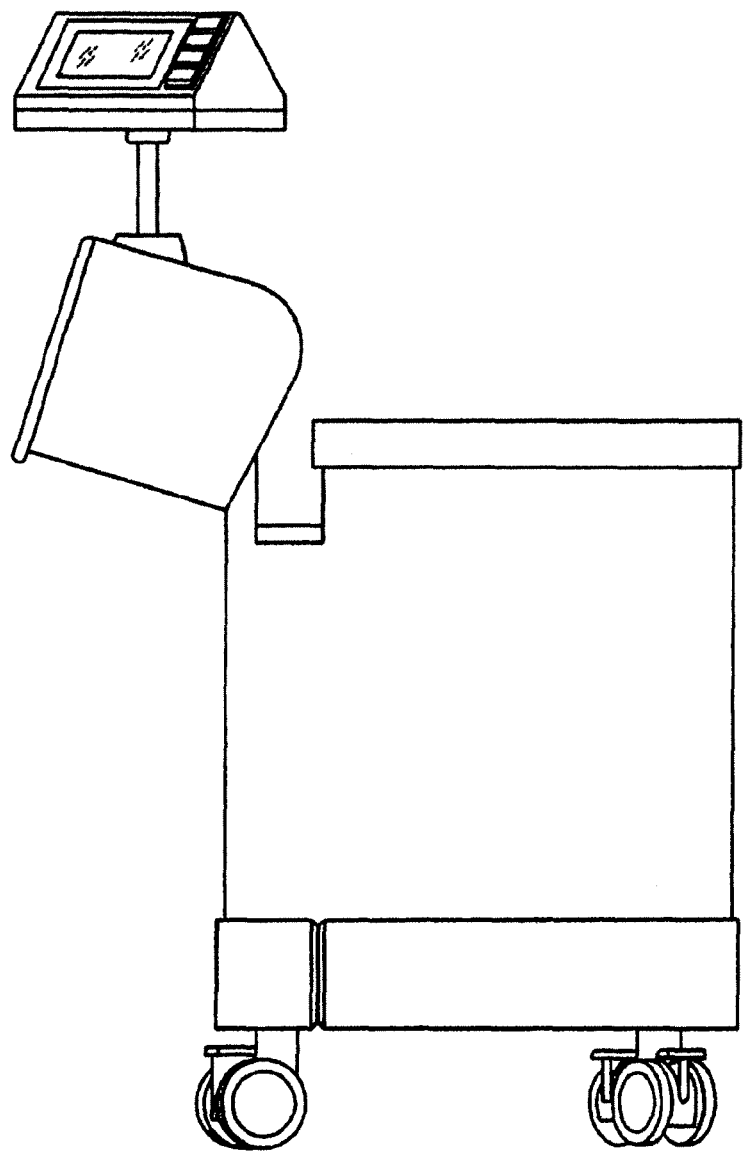
FIG. 37 is a right-side elevational view of the system shown in FIG. 34.
Figure 38:
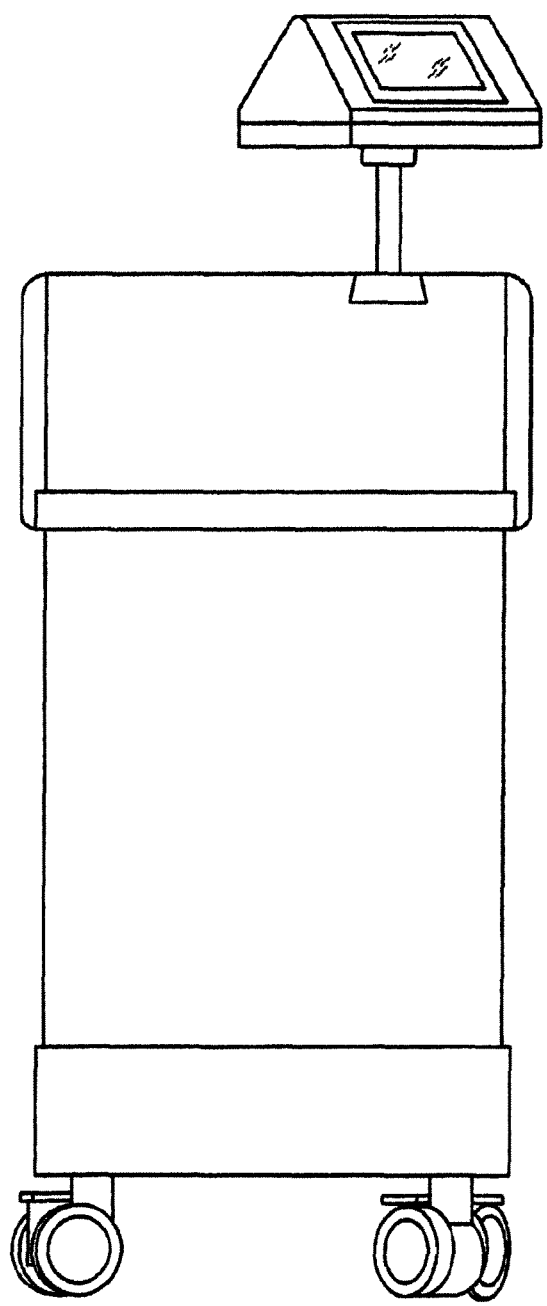
FIG. 38 is a rear elevational view of the system shown in FIG. 34.
Figure 39:
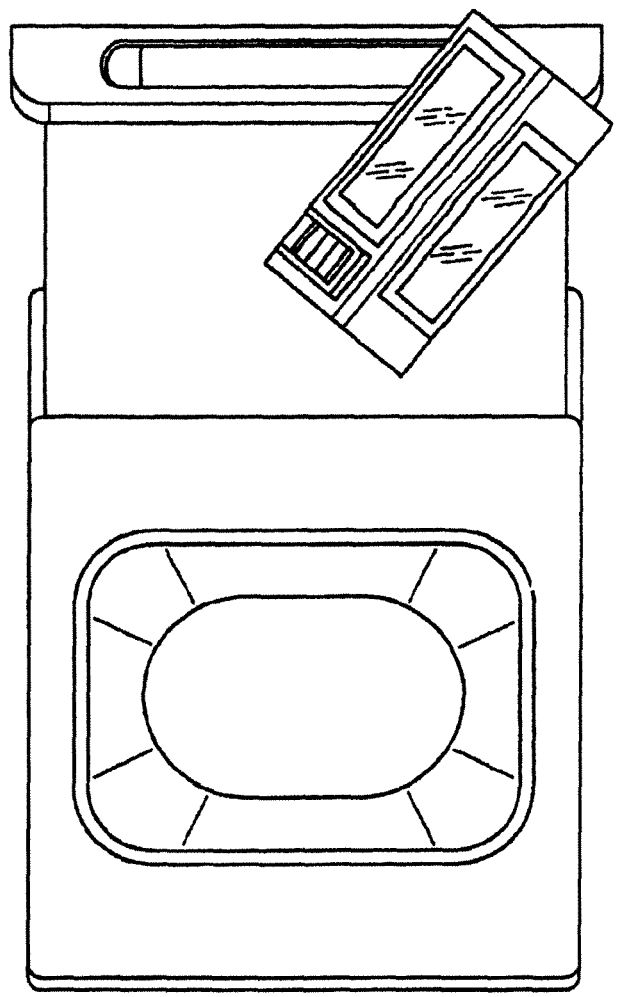
FIG. 39 is a top plan view of the system shown in FIG. 34.
Figure 40:
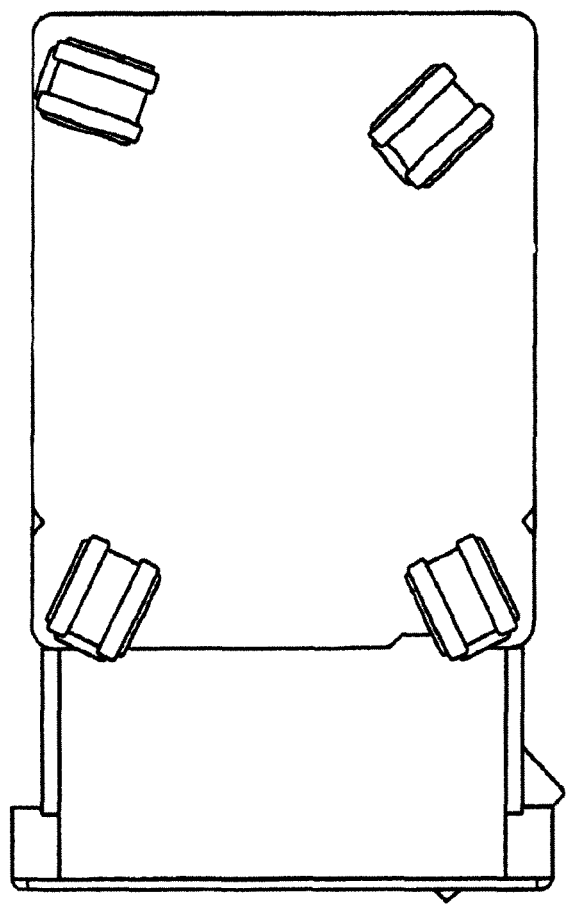
FIG. 40 is a bottom plan view of the system shown in FIG. 34.

In the embodiment shown in FIG. 33, a double loop bridge antenna 670 is combined with two antennas 690 and 694 with the bridge having a tuning circuit 682. Antennas 690 and 694 have tuning circuits 692 and 696 respectively. The bridge antenna 670 may generate a field at an angle to the rotating field created by antennas 690 and 694.

In one embodiment, the apparatus may have one object detection zone containing antennas. The antennas may be used as either entry detection zone antennas or exit detection zone antennas. For example, a switch may be used to indicate to control circuitry 30 whether the antennas will function as entry detection zone antennas or as exit detection zone antennas. The switch may be a mechanical switch, an infrared switch, proximity switch or any other suitable switch. An individual switch or a combination of switches may be used. Alternatively, control circuitry 30 may be programmed to function as entry detection zone antennas or exit detection zone antennas based on contextual cues.

It will be appreciated that a variety of materials, configurations and properties may be employed in the antennas and identifiers of the present invention. With respect to the antennas, they may be made of copper or other materials having high conductivity.

An identifier on an object to be monitored may, in certain embodiments, be an RF tag or a microchip that utilizes any other suitable technology to identify objects. Alternatively, an object may be equipped to spontaneously emit electromagnetic waves containing identification information, which may be read by antennas. A bar code may also be attached to an object in order to identify it. An identifier of the invention may be one that works through pattern recognition technology, whereby a visual image of the object is obtained, and control circuitry algorithms are utilized to identify the object from its image. Those of skill in the art will recognize that any of these or other suitable identifiers or combination of identifiers may be used in the present invention.

With respect to identifiers, RF tags are one embodiment. Identifiers such as RF tags may have various shapes and dimensions. The tags and associated antennas may be operated in a range of frequencies. While tags are generally rigid, they may be made to be somewhat flexible. An identifier may be attached to an object by stitching the identifier between two layers of the object around the periphery on all four sides to resist movement of the tag with respect to the object. In the alternative, they may be attached by alternate means such as suitable adhesives, such as by epoxies, resins and cyanoacrylates, for example. The tags may be passive and would therefore not function if not in a detection field tuned to their frequency.

Figure 41:
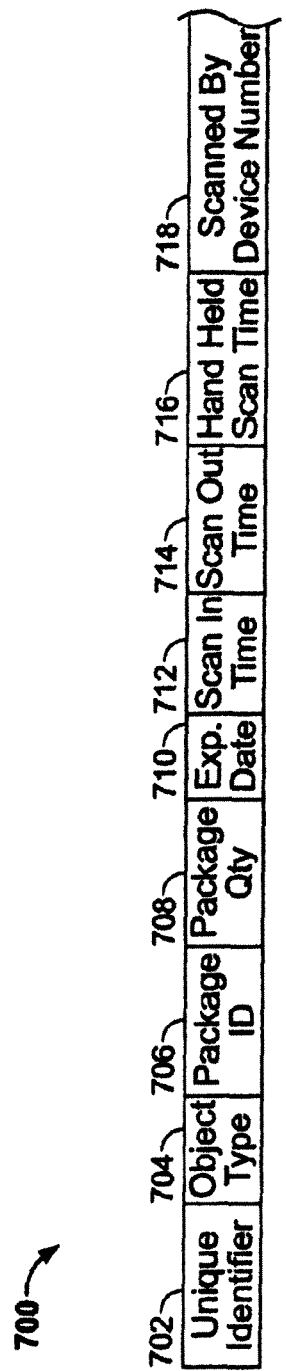
FIG. 41 shows a memory structure of an RF tag in one embodiment of the invention.

RF tags used in the system may have information stored to specific memory segments. For example, FIG. 41 shows an RF tag memory 700. RF tag memory 700 may be programmed to store information identifying an object. For example, memory segment 700 may store information in memory segments 702, 704, 706, 708, 710, 712, 714, 716 and 718. The information may include the object's unique identifier (memory segment 702), the type of object (memory segment 704), the package identity (memory segment 706), the number of objects in a package (memory segment 708), the object expiration date (memory segment 710), the time the object was scanned in (memory segment 712), the time the object was scanned out (memory segment 714), the time an antenna, such as the handheld antenna, scanned the object (memory segment 716), and the identifying number of the antenna used to scan the object (memory segment 718). RF tag memory 700 may store additional information such as whether the object has already been scanned in or scanned out, a flag indicating whether the object has been scanned in or scanned out, the date of manufacture of the object and any other desirable information.

Figure 42:
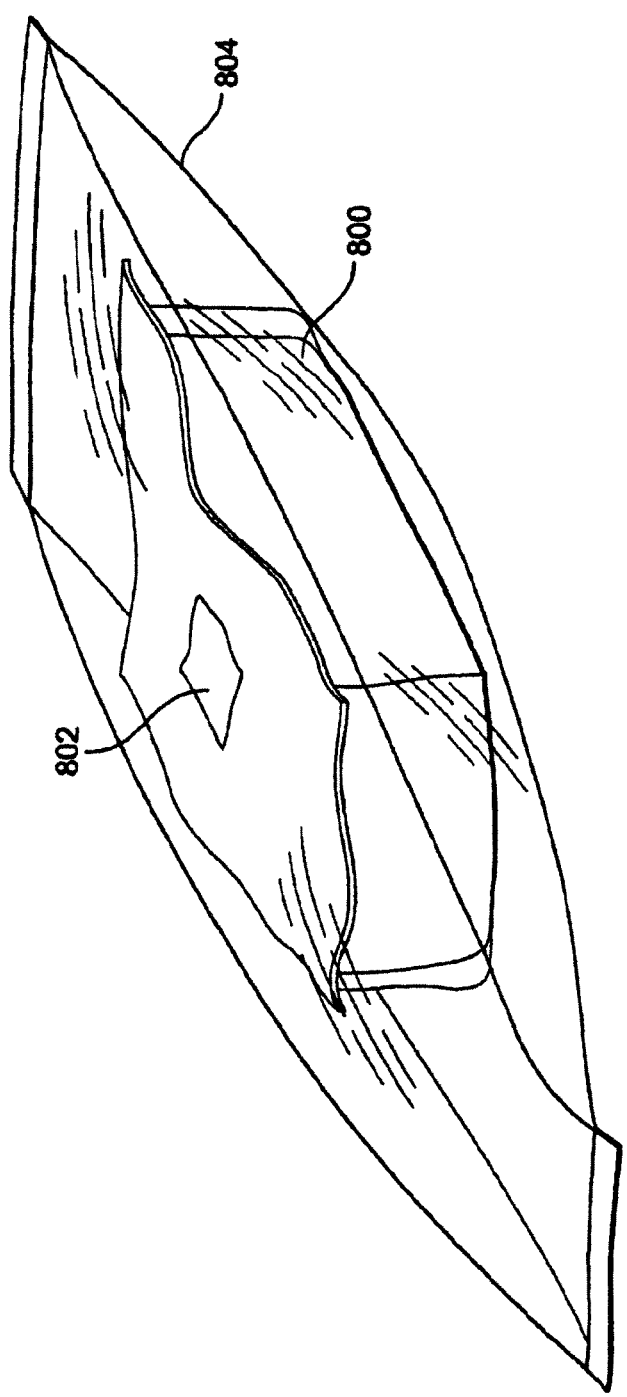
FIG. 42 shows a protective outer wrapping or covering of a package of objects in one embodiment of the invention.

Identifiers may be protected from deterioration and accidental or intentional data corruption. For example, identifiers may be protectively encapsulated in inert biocompatible plastics. As the protective plastic materials in which identifiers are encapsulated may be water-impermeable, fluidimpermeable and gas-impermeable, the identifiers can resist deterioration when exposed to gas sterilization methods. Identifiers may also be encapsulated in an outer material that has electromagnetic shielding properties in order to prevent data corruption due to the presence of other electromagnetic waves. For example, FIG. 42 shows package of objects in one embodiment of the invention with a protective outer wrapping or covering, such as a protective encapsulation. In FIG. 42, package 800 may have identifier 802 which contains information identifying it. Package 800 may also have a protective encapsulation 804, which may be a protective plastic material or a material with electromagnetic shielding properties.

Figure 43:
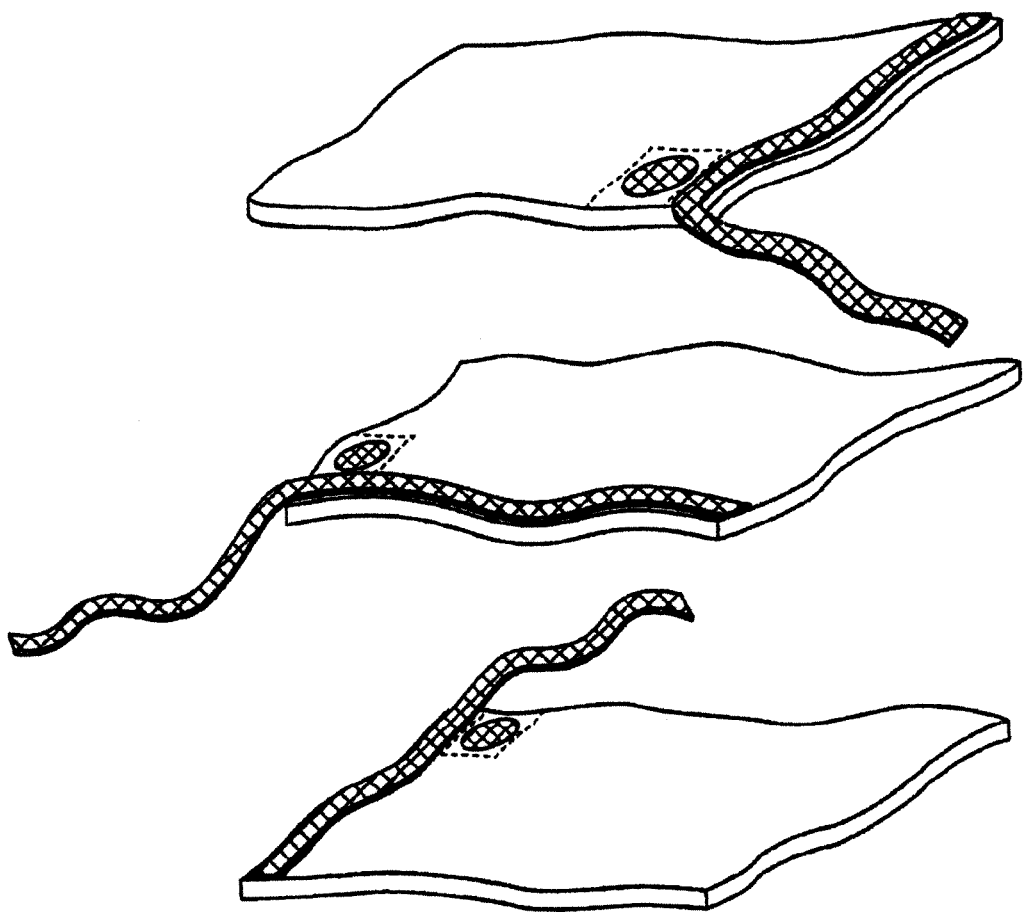
FIG. 43 shows adjacent objects utilizing a placement of tags of one embodiment of the invention.
Figure 44:
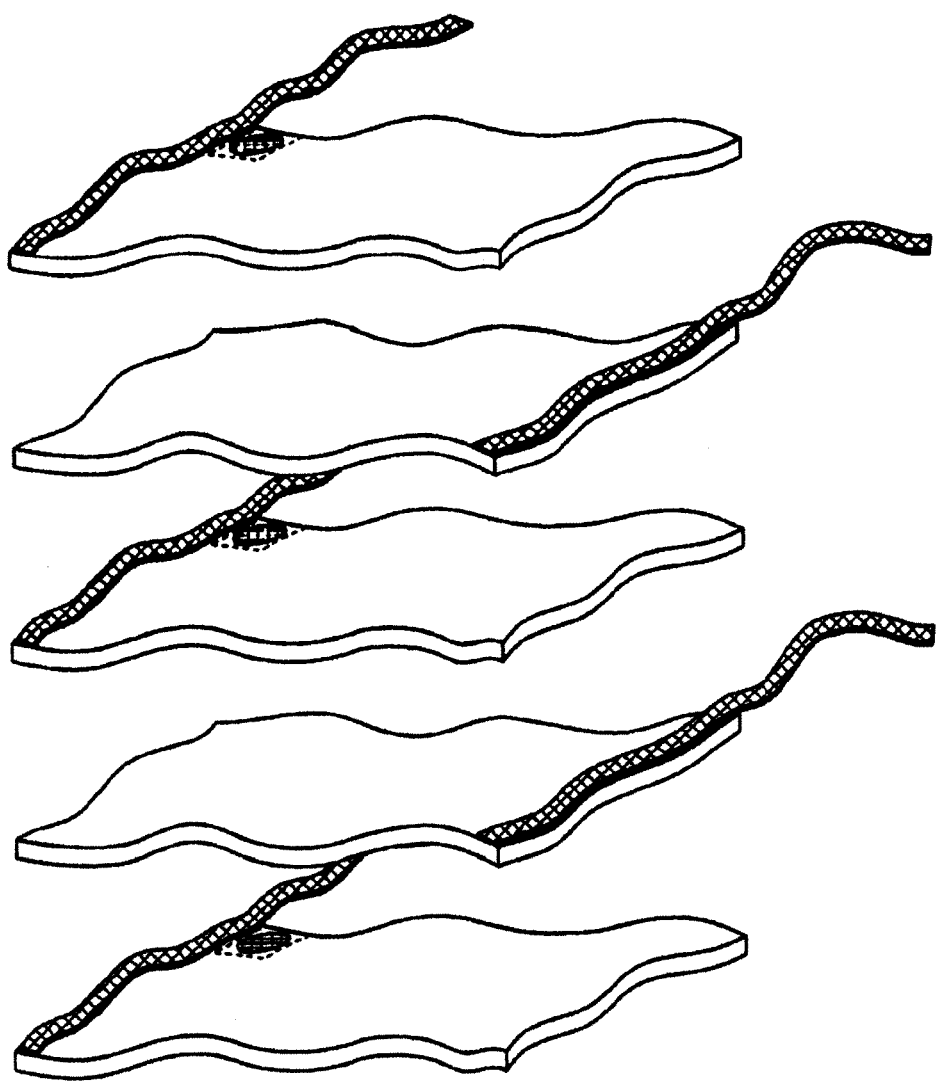
FIG. 44 shows adjacent objects utilizing a placement of tags of one embodiment of the invention.

Identifiers may also be protected from electromagnetic coupling with other identifiers, preventing a reduction in reading range. The effects of electromagnetic coupling are generally greatest when identifiers are packed in close proximity and are stacked center-on-center. In one embodiment, electromagnetic coupling between identifiers may be reduced by positioning identifiers at strategic locations on objects. The identifier for each object may be positioned such that when each object is packaged with another object, there will be maximum spacing between their identifiers. For example, identifiers may be placed at alternating corners of objects so that there is maximum vertical spacing between tags as shown in FIGS. 43 and 44. As shown in FIG. 43, the objects may be packaged with all their identifiers facing the same vertical direction. Alternatively, the objects may be packaged such that every other object has their identifier facing in the same vertical direction, as shown in FIG. 44.

Figure 45:
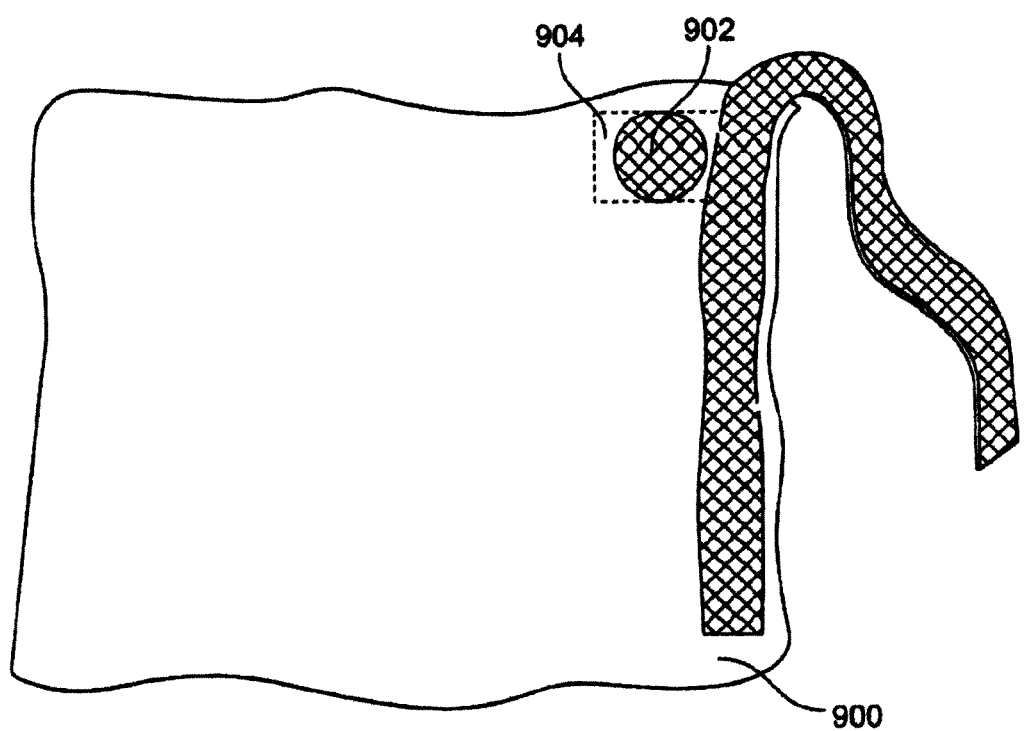
FIG. 45 shows an object with a padded pocket of one embodiment of the invention.

In another embodiment, identifiers may have protective covering in order to minimize electromagnetic coupling. The protective covering may have characteristics and dimensions that helps to reduce electromagnetic coupling when placed between identifiers. For example, the protective covering may be a padded pocket which is thick enough so that, when placed between two tags stacked center-to-center, it separates the tags and minimizes electromagnetic coupling. FIG. 45 shows an object 900 with an identifier 902. Object 900 may also have a protective covering 904 to reduce electromagnetic coupling. For example, absorbent material used in the main body of object 900 may be thicker around identifier 902, as shown by the dotted line marking the perimeter of protective covering 904.

Figure 46A:
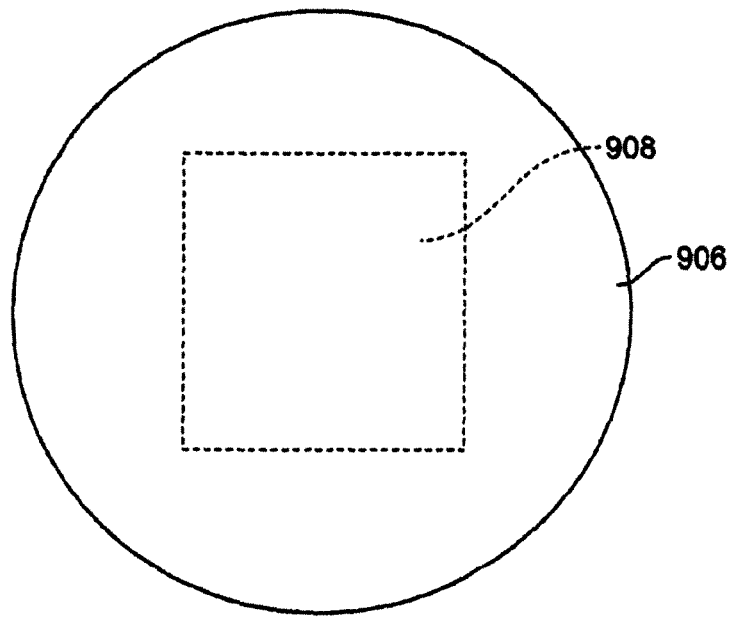
FIGS. 46a and 46b show a top view and a side view of an encapsulating covering of one embodiment of the invention.
Figure 46B:
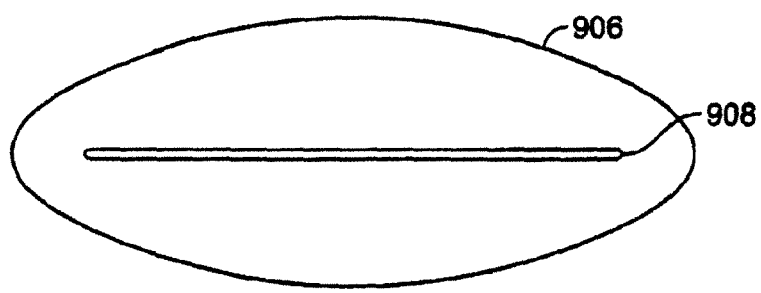

In yet another embodiment, identifiers may be encapsulated to minimize electromagnetic coupling. The encapsulation used may be of different shapes. For example, a disk-shaped encapsulation may be used as is shown in FIGS. 46*a* and 46*b*. As can be seen in FIG. 46*a*, the disk-shaped encapsulation 906 may be used to enclose identifier 908. The disk may have a plane parallel to that of the antennas in the system in order to aid detection of the identifier it encapsulates. The disk may also be chosen to be thick enough so that electromagnetic coupling is reduced to an acceptable degree when it is placed in between tags.

Figure 47A:
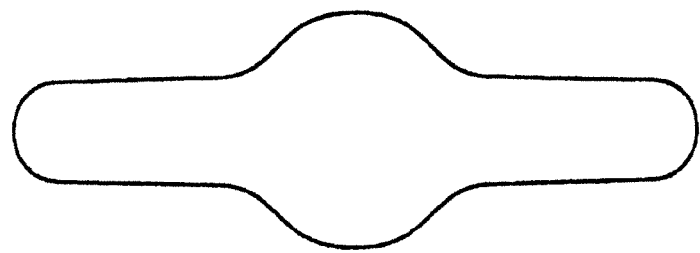
FIGS. 47a and 47b show an encapsulating covering with a bump feature of one embodiment of the invention.
Figure 47B:
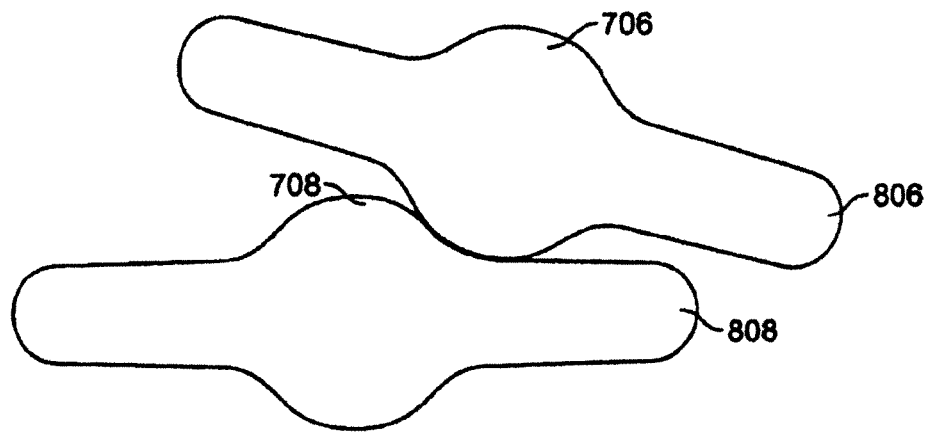

The disk may also be designed in order to further electromagnetic coupling. For example, the disk may have a "bump" at its center and may be placed at the center of the identifier as shown in FIG. 47*a*. It can also be seen from FIG. 47*b* that having a plurality of identifiers contained in disks with bumps at their centers may reduce the possibility of center-on-center stacking between tags. This is because, as seen in FIG. 47*b*, disk-shaped encapsulations 806 and 808 are prevented from lying in a center-to-center position due to their bumps 706 and 708. Other modifications and variations of this feature may be used.

The system provided by the present invention may be used alone or in conjunction with other systems. If the system is used alone as a stand-alone device in a surgical field, it may be set up to communicate with other stand-alone devices. This may facilitate the compilation of information. Alternatively, a single stand-alone device may be adapted to store information across multiple surgical fields and to combine that information in a way that helps the user track the total number of objects in multiple surgical fields. For example, the user may be able to determine the total number of a particular object utilized in different surgical fields. Control circuitry 30 may also be set up to collect all the data on the objects detected by the individual stand-alone devices, and to compile the data in one database.

The methods and apparatus of the present invention may be used either alone, or in conjunction with other systems, methods and apparatus. Examples of systems, methods and apparatus that may be used in conjunction with the present invention are disclosed, e.g., in U.S. patent application Ser. No. 08/286,413, now U.S. Pat. No. 5,650,596, U.S. patent application Ser. No. 08/833,387, now U.S. Pat. No. 5,923,001, U.S. patent application Ser. No. 10/411,885, now U.S. Pat. No. 6,998,541 and United States Patent Publication Number US2006/0044137, each of which is incorporated by reference in its entirety.

It will be appreciated that the present invention provides a number of efficient methods for effectively and accurately controlling the monitoring, detection, counting, identification and in some cases, further characterization of objects entering and exiting a surgical field or surgical site, so as to avoid inadvertent retention of an object within a patient. In one embodiment, a patient is scanned as a result of a lower array of antennas underlying the patient to determine if any objects are in a patient, particularly immediately prior to closing of the patient at the end of the surgical procedure. A further refinement of this embodiment involves the use of an overlying upper antenna or array of antennas which will more precisely define the detection field at or adjacent the surgical site. In one embodiment, an object entry detection zone and an object exit detection zone cooperate to monitor the use of surgical objects.

Whereas particular embodiments of the invention have been described herein for purposes of illustration, it will be evident to those skilled in the art that numerous variations of the details may be made without departing from the invention as set forth in the appended claims.

What is claimed is:

1. A method of monitoring a surgical operation, the method comprising:
   providing a monitoring system for identifying a surgical object having an RF tag including an unique identifier, the monitoring system comprising a base supported on wheels, a visual display unit supported by the base, a first scanner including an antenna supported by the base, a second scanner supported by the base and different from the first scanner, and control circuitry supported by the base and in communication with the visual display unit, the first scanner, and the second scanner;
   positioning the base relative to a surgical field;
   scanning the surgical object with the first scanner to identify the surgical object by the unique identifier and displaying on the visual display unit information relating to the surgical object;
   scanning the surgical object with the second scanner to identify the surgical object by the unique identifier and displaying information on the visual display unit relating to the surgical object scanned with the second scanner.

2. The method of monitoring of claim 1, further comprising determining the surgical object as present within the surgical field after scanning the surgical object with the first scanner.

3. The method of monitoring of claim 2, further comprising initiating an alarm in an event that at an end of a surgical procedure when the surgical object has been determined as within the surgical field and has not been determined as removed from within the surgical field.

4. The method of monitoring of claim 3, wherein the second scanner is movable within the surgical field independent of the base; wherein scanning with the second scanner comprises moving the second scanner relative to a patient within the surgical field; and further comprising repeating the step of scanning with the second scanner subsequent to initiating the alarm.

5. The method of monitoring of claim 1 wherein the step of scanning the surgical object with the second scanner further comprises emitting an RF field into the surgical field with the second scanner; receiving a response from the RF tag of the surgical object with the second scanner; electronically communicating a signal from the second scanner to the control circuitry; and determining a location of the surgical object based on the signal received from the second scanner.

6. The method of monitoring of claim 5, wherein the second scanner is movable within the surgical field independent of the base, and wherein scanning with the second scanner comprises moving the scanner relative to a patient within the surgical field.

7. The method of monitoring of claim 1, further comprising providing a third scanner including an antenna, different from the first and second scanners, operatively associated with the base and in communication with the control circuity; and scanning the surgical object with the third scanner to identify the surgical object by the unique identifier.

8. The method of monitoring of claim 7, wherein scanning with first scanner determines the surgical object as present within the surgical field and wherein scanning with the third scanner determines the surgical object as removed from within the surgical field.

9. The method of monitoring of claim 8, wherein the third scanner is a collection container such that scanning with the third scanner is performed while the surgical object is disposed within the collection container.

10. A method of operating a surgical monitoring system, the surgical monitoring system comprising a base supported on wheels, a visual display unit supported by the base, a first scanner including an antenna supported by the base, a second scanner supported by the base and different from the first scanner, and control circuitry supported by the base in communication with the visual display unit, the first scanner and the second scanner, the method comprising:
  positioning the base relative to a surgical field;
  operating the control circuitry to scan using the first scanner to identify a unique identifier of a surgical object, the system displaying information on the visual display unit subsequent to the identification of the surgical object by the first scanner;
  operating the control circuitry to scan using the second scanner to identify the unique identifier of the surgical object, the system displaying information on the visual display unit subsequent to the identification of the surgical object by the second scanner.

11. The method of operating of claim 10, the control circuitry determines the surgical object as present within the surgical field after identification of the surgical object by the first scanner.

12. The method of operating of claim 10, wherein the step of operating the control circuitry to scan using the second scanner comprises emitting an RF field into the surgical field from the second scanner; receiving a response signal from the RF tag of the surgical object with the second scanner; electronically communicating a signal from the second scanner to the control circuitry; and identifying the surgical object based on the signal received from the second scanner.

13. The method of operating of claim 12, further comprising the control circuitry initiating an alarm in an event that at an end of a surgical procedure when the surgical object has been determined as within the surgical field and has not been determined as removed from within the surgical field.

14. The method of monitoring of claim 13, wherein the second scanner is movable within the surgical field independent of the base; wherein operating the control circuitry to scan with the second scanner occurs during movement of the second scanner relative to a patient within the surgical field; and the method further comprising repeating the step of operating the control circuitry to scan with the second scanner subsequent to initiating the alarm.

15. The method of operating of claim 12, wherein the second scanner is movable within the surgical field independent of the base, and wherein operating the control circuitry to scan with the second scanner occurs during movement of the second scanner relative to a patient within the surgical field.

16. The method of operating of claim 10, wherein the surgical monitoring system further comprises a third scanner including an antenna, different from the first and second scanners, operatively associated with the base and in communication with the control circuity; the method further comprising operating the control circuitry to scan using the third scanner to identify the surgical object by the unique identifier, the system displaying information on the visual display unit subsequent to the identification of the surgical object by the third scanner.

17. The method of operating of claim 16, wherein operating the control circuitry to scan with the first scanner determines the surgical object as present within the surgical field and wherein operating the control circuitry to scan with the third scanner designates the surgical object as removed from within the surgical field.

18. The method of operating of claim 16, wherein the third scanner is a collection container such that operating the control circuitry to scan with the third scanner is performed while the surgical object is disposed within the collection container.

19. A method of identifying and tracking a surgical object having an RF tag including an unique identifier, the method comprising:
  providing a monitoring system comprising a base supported on wheels, a visual display unit supported by the base, a first scanner including an antenna supported by the base, a second scanner supported by the base and different from the first scanner, and control circuitry supported by the base and in communication with the visual display unit, the first scanner, and the second scanner;
  positioning the base relative to a surgical field;
  displaying object entry data on the visual display unit subsequent to the identification of the surgical object by the unique identifier after a first scanning of the surgical object by one of the first and second scanners, wherein the object entry data determines the surgical object to be within the surgical field;

displaying object exit data on the visual display unit upon identification of the surgical object by the unique identifier after a second scanning of the surgical object by one of the first and second scanners, wherein the object exit data determines the surgical object to be removed from the surgical field.

20. The method of identifying and tracking a surgical object of claim 19, wherein the monitoring system further comprises a third scanner including an antenna, different from the first and second scanners, operatively associated with the base and in communication with the control circuitry; wherein the third scanner is movable within the surgical field independent of the base; the method further comprising the step of displaying a visual alarm upon identification of the surgical object by the unique identifier after a scan using the third scanner, wherein the scan using the third scanner comprising moving the third scanner relative to a patient within the surgical field.

\* \* \* \* \*